United States Patent
Truckai et al.

(10) Patent No.: US 6,821,275 B2
(45) Date of Patent: Nov. 23, 2004

(54) VOLTAGE THRESHOLD ABLATION APPARATUS

(76) Inventors: Csaba Truckai, 19566 Arden Ct., Saratoga, CA (US) 95070; Bruno Strul, 485 Cervantes Rd., Portola Valley, CA (US) 94028

( * ) Notice: Subject to any disclaimer, the term of this patent is extended or adjusted under 35 U.S.C. 154(b) by 45 days.

(21) Appl. No.: 10/135,135

(22) Filed: Apr. 30, 2002

(65) Prior Publication Data

US 2004/0010249 A1 Jan. 15, 2004

Related U.S. Application Data

(63) Continuation of application No. 09/631,040, filed on Aug. 1, 2000, now Pat. No. 6,413,256.

(51) Int. Cl.[7] ............................................. A61B 18/18
(52) U.S. Cl. ............................. 606/41; 606/40; 606/49; 606/50
(58) Field of Search .......................... 606/40–42, 49–50

(56) References Cited

U.S. PATENT DOCUMENTS

| | | | |
|---|---|---|---|
| 4,060,088 A | 11/1977 | Morrison, Jr. et al. | |
| 4,781,175 A | 11/1988 | McGreevy et al. | |
| 5,207,675 A | 5/1993 | Canady | |
| 5,256,138 A | * 10/1993 | Burek et al. | ............ 606/42 |
| 5,669,907 A | 9/1997 | Platt, Jr. et al. | |
| 5,776,092 A | 7/1998 | Farin et al. | |
| 5,849,010 A | 12/1998 | Wurzer et al. | |
| 6,013,075 A | 1/2000 | Avramenko et al. | |
| 6,039,736 A | 3/2000 | Platt, Jr. | |
| 6,142,992 A | 11/2000 | Cheng et al. | |
| 6,235,020 B1 | 5/2001 | Cheng et al. | |
| 6,296,636 B1 | 10/2001 | Cheng et al. | |
| 6,419,674 B1 | * 7/2002 | Bowser et al. | ............ 606/45 |
| 2003/0014051 A1 | 1/2003 | Woloszko | |

* cited by examiner

*Primary Examiner*—Roy D. Gibson
(74) *Attorney, Agent, or Firm*—Townsend and Townsend and Crew LLP

(57) ABSTRACT

A method and apparatus for treating tissue using an electrosurgical system. The system includes an electrosurgical system having an RF generator, a treatment electrode electrically coupled to the RF generator and positioned in contact with target tissue to be treated, and a spark gap switch positioned between the RF generator and the target tissue. The spark gap includes a threshold voltage and is configured to prevent conduction of current from the RF generator to the tissue until the voltage across the spark gap reaches the threshold voltage.

The method includes the steps of using the RF generator to apply a voltage across the spark gap switch, the spark gap switch causing conduction of current from the RF generator to the target tissue once the voltage across the spark gap reaches the threshold voltage.

23 Claims, 19 Drawing Sheets

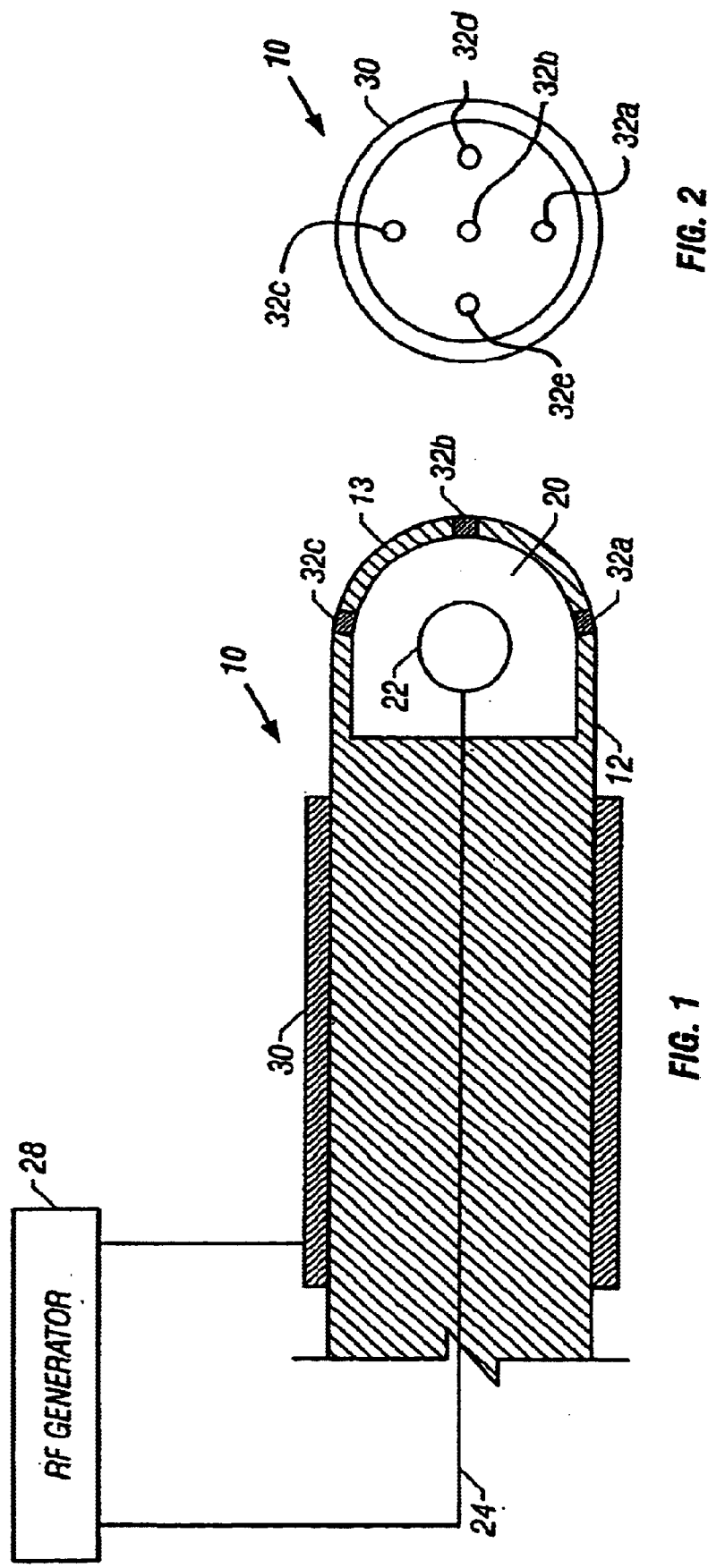

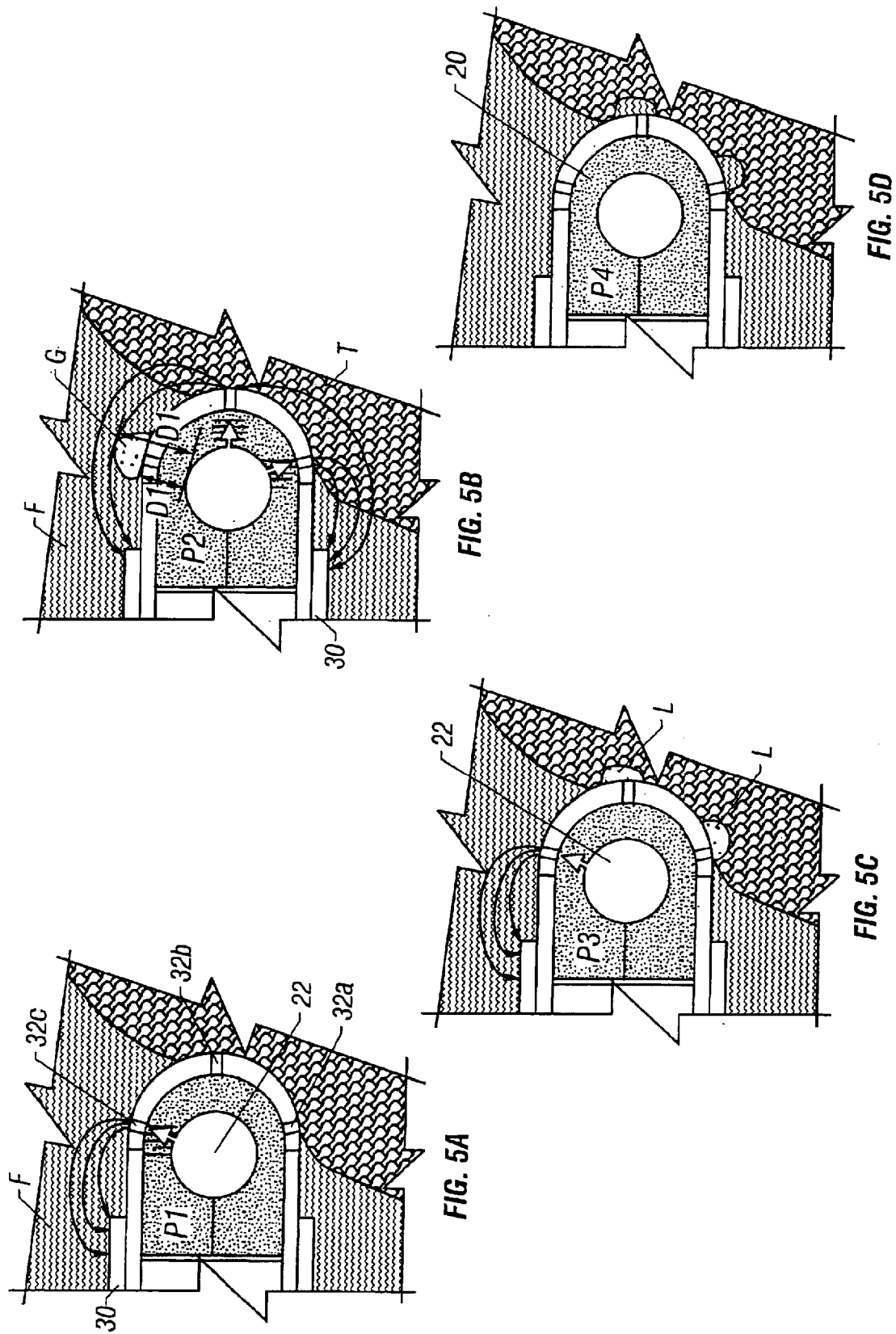

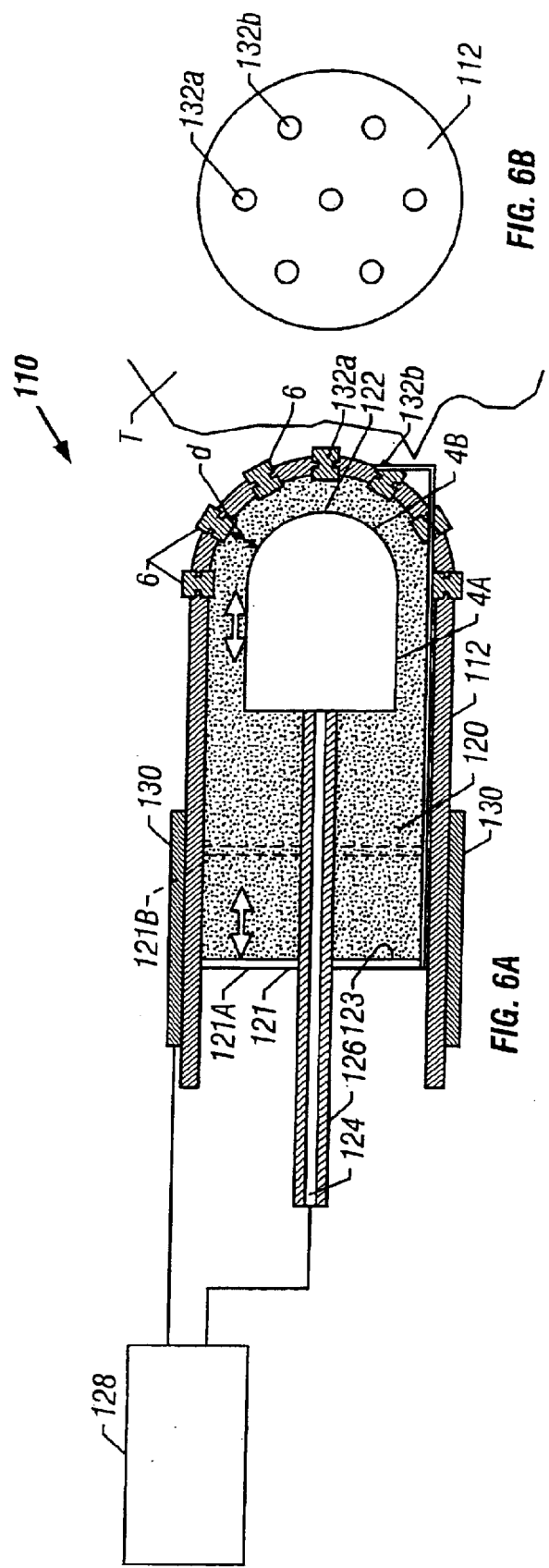

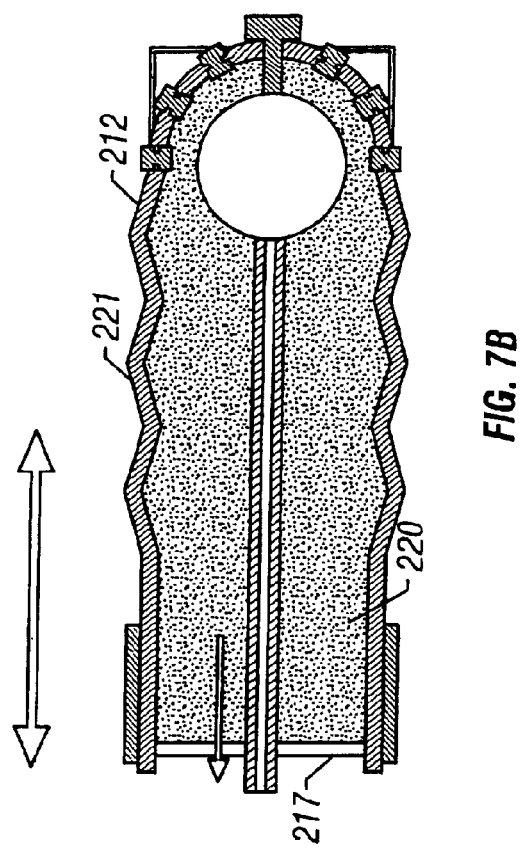
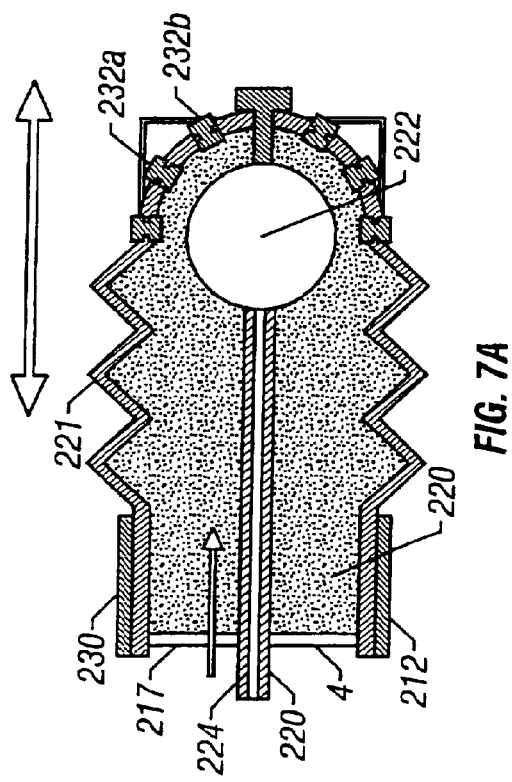

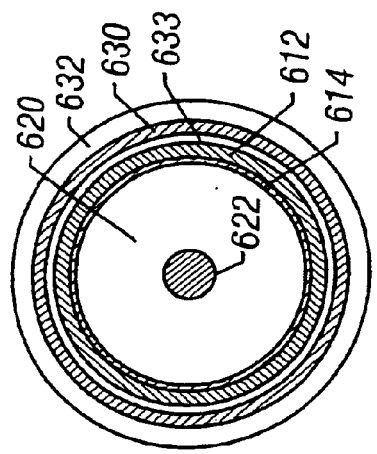
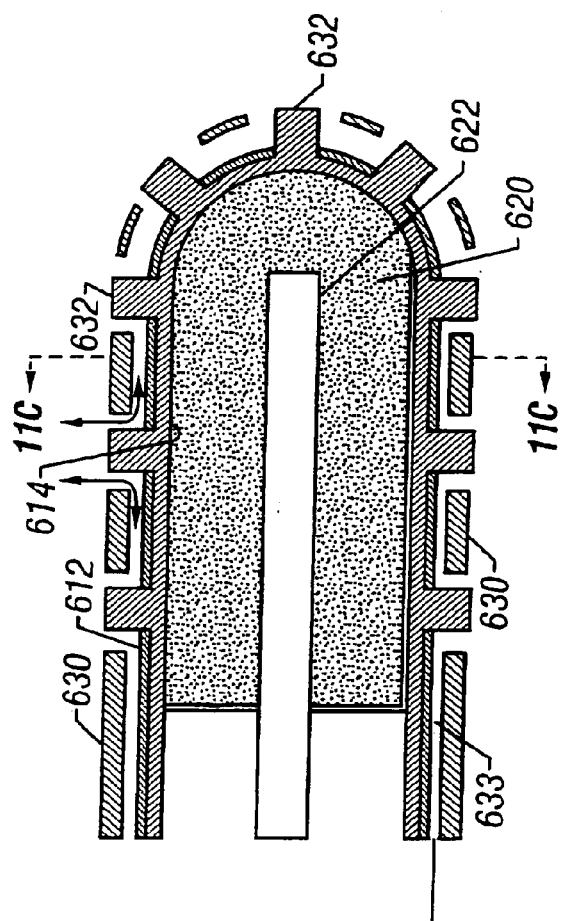

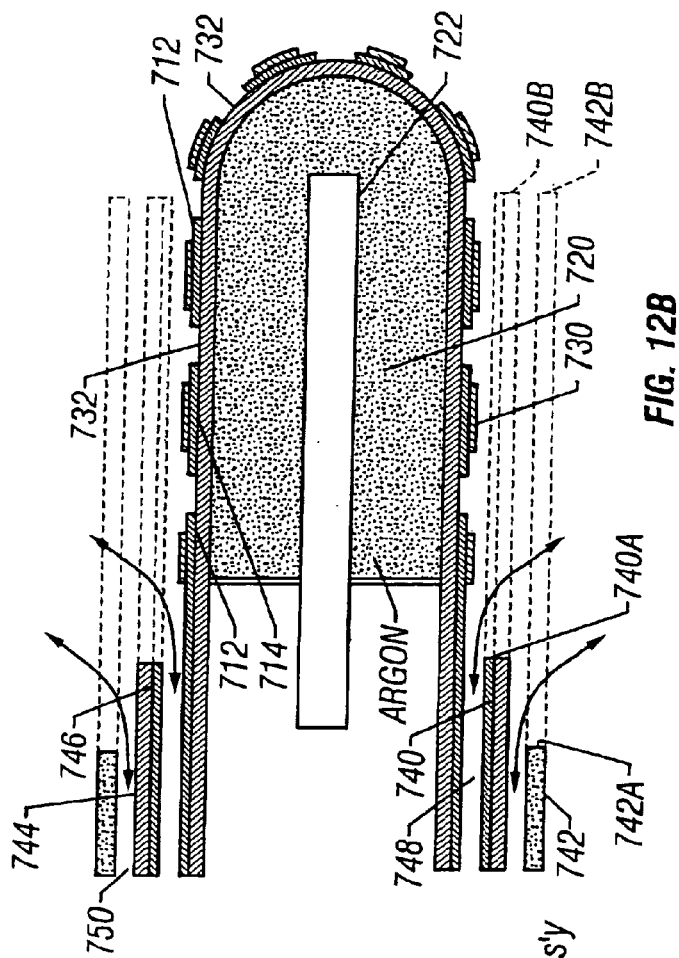
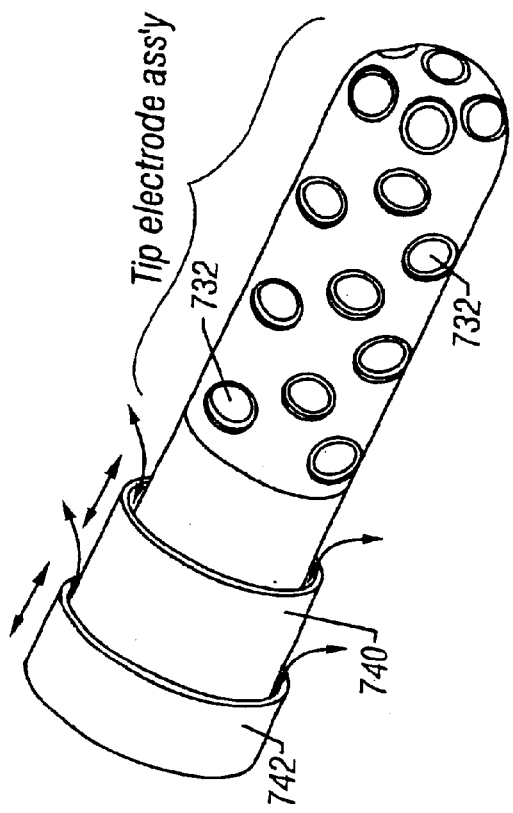
FIG. 12B
FIG. 12A

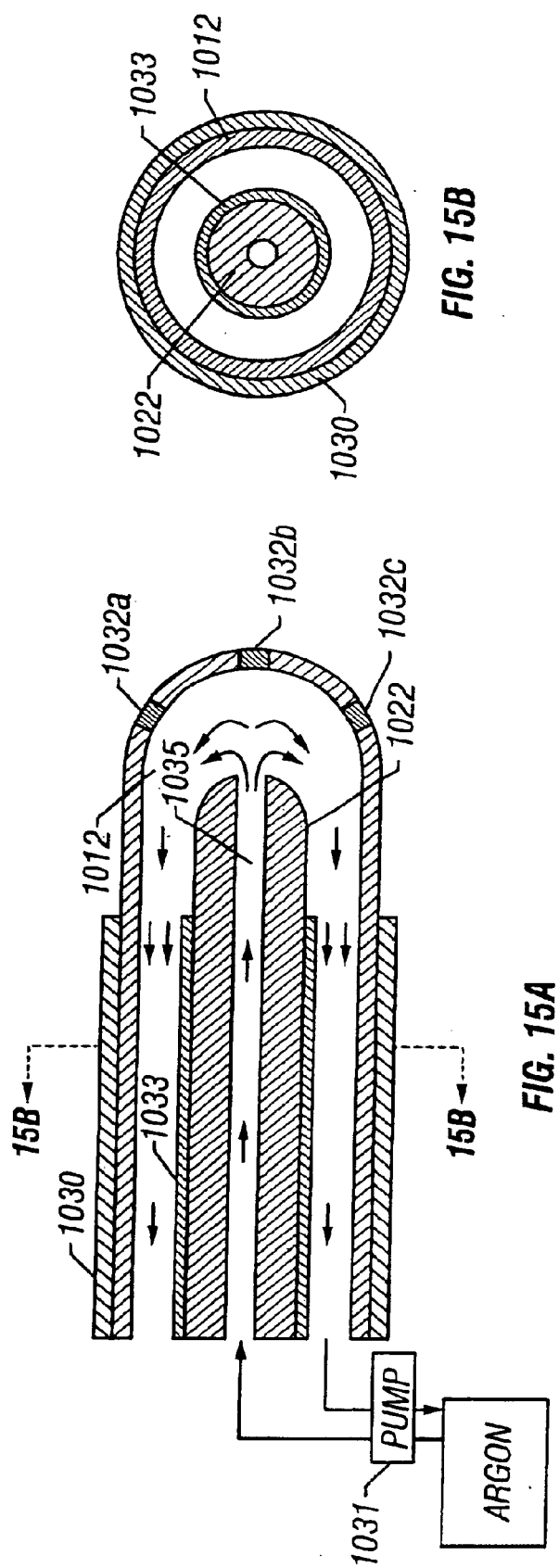

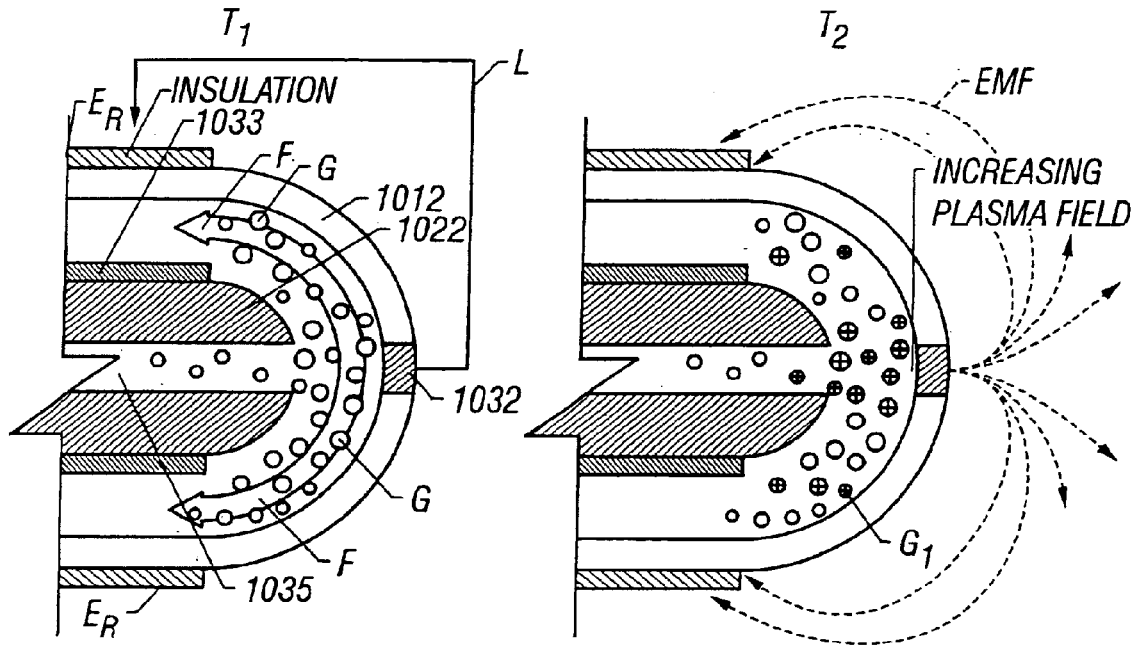

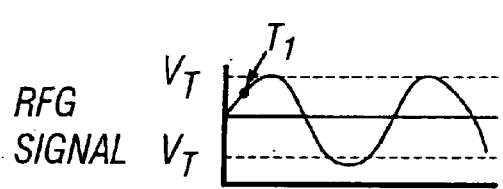

VT = MINIMUM V POTENTIAL TO REACH IONIZATION ⇒ CONVECTION

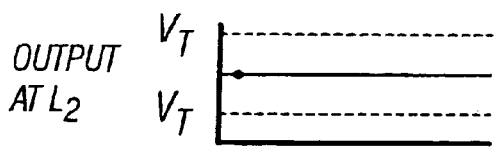

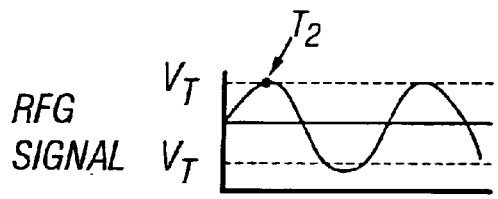

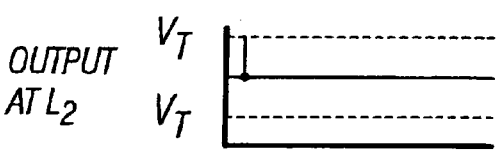

THE POTENTIAL GENERATED BETWEEN $E_1$ AND $E_A$ ⇒ $P_1$
$P_1 < P_{VT}$ ⇒ NO CONDUCTION

ASSUMPTION $E_R$ AND $E_A$ DIRECTLY WIRED TO LOAD BOX
*NO LOAD VAPORIZATION

FIG. 16A

POTENTIAL BETWEEN $E_1$ AND $E_A$ = $P_2$
$P_2 > P_{VT}$ ⇒ GAS IONIZATION
ABLATION ⇐ CONDUCTION

MORE $G_1$ GENERATED BETWEEN $E_1$ AND $E_A$ THAN CARRIED AWAY BY THE GAS FLOW ⇒ EXPANDING PLASMA

FIG. 16B

$E_1$ AND $E_A$ DISTANCE EFFECT ON
OUTPUT MEASURED AT LOAD
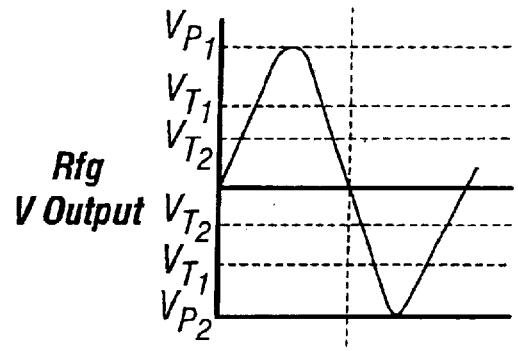
$$\frac{D_1}{D_2} \simeq \frac{I_1}{I_2} \simeq \frac{V_{T_1}}{V_{T_2}} \quad F=CONST$$
②
$$\frac{D_1}{D_2} \simeq \frac{I_1}{I_2}$$
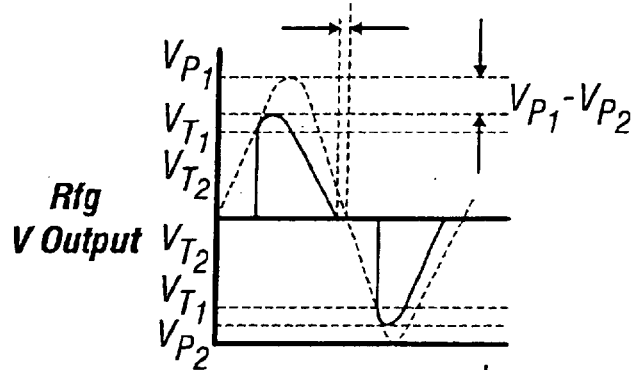
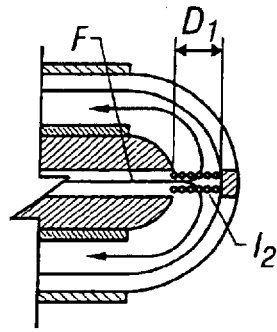
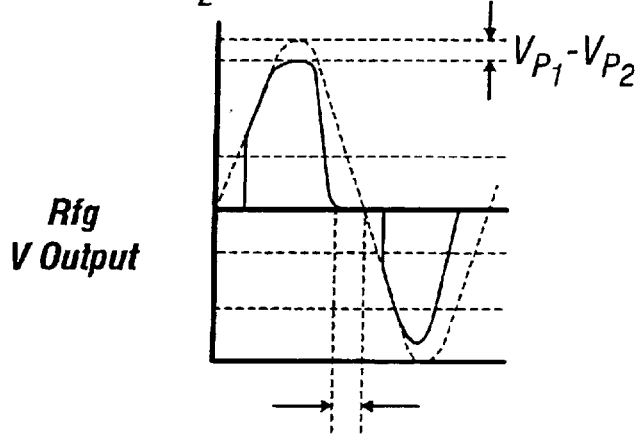
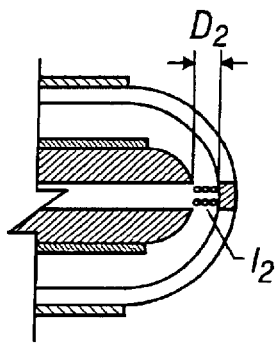
FIG. 18

WHERE:
D1 DISTANCE BETWEEN 1122c AND 1132
D2 DISTANCE BETWEEN 1122b AND 1132
D3 DISTANCE BETWEEN 1122a AND 1132
D1 <D3<D3
V1 <V3<V2
V1 THRESHOLD VOLTAGE (1)
V2 THRESHOLD VOLTAGE (2)
V3 THRESHOLD VOLTAGE (3)

VOLTAGE THRESHOLD ABLATION APPARATUS

CROSS REFERENCE TO RELATED APPLICATION

This is a continuation of U.S. patent application Ser. No. 09/631,040 filed on 1 Aug. 2000 now U.S. Pat. No. 6,413,256 and entitled Voltage Threshold Ablation Method and Apparatus.

FIELD OF THE INVENTION

The present invention relates to the field of electrosurgery, and more particularly to methods for ablating, cauterizing and/or coagulating body tissue using radio frequency energy.

BACKGROUND OF THE INVENTION

Radio frequency ablation is a method by which body tissue is destroyed by passing radio frequency current into the tissue. Some RF ablation procedures rely on application of high currents and low voltages to the body tissue, resulting in resistive heating of the tissue which ultimately destroys the tissue. These techniques suffer from the drawback that the heat generated at the tissue can penetrate deeply, making the depth of ablation difficult to predict and control. This procedure is thus disadvantageous in applications in which only a fine layer of tissue is to be ablated, or in areas of the body such as the heart or near the spinal cord where resistive heating can result in undesirable collateral damage to critical tissues and/or organs.

It is thus desirable to ablate such sensitive areas using high voltages and low currents, thus minimizing the amount of current applied to body tissue.

SUMMARY OF THE INVENTION

The present invention is a method and apparatus for treating tissue using an electrosurgical system. The system includes an electrosurgical system having an RF generator, a treatment electrode electrically coupled to the RF generator and positioned in contact with target tissue lo be treated, and a spark gap switch positioned between the RF generator and the target tissue. The spark gap includes a threshold voltage and is configured to prevent conduction of current from the RF generator to the tissue until the voltage across the spark gap reaches the threshold voltage.

A method according to the present invention includes the steps of using the RF generator to apply a voltage across the spark gap switch, the spark gap switch causing conduction of current from the RF generator to the target tissue once the voltage across the spark gap reaches the threshold voltage.

BRIEF DESCRIPTION OF THE DRAWINGS

FIG. 1 is a cross-sectional side elevation view of a first embodiment of an ablation device utilizing principles of the present invention.

FIG. 2 is an end view showing the distal end of the device of FIG. 1.

FIGS. 5A through 5D are a series of cross-sectional side elevation views of the ablation device of FIG. 1, schematically illustrating use of the device to ablate tissue.

FIG. 6A is a cross-sectional side view of a second embodiment of an ablation device utilizing principles of the present invention.

FIG. 6B is an end view showing the distal end of the device of the device of FIG. 6A.

FIGS. 7A and 7B are cross-sectional side elevation view of a third embodiment of an ablation device utilizing principles of the present invention. In FIG. 7A, the device is shown in a contracted position and in FIG. 7B the device is shown in an expanded position.

FIG. 11B is a cross-sectional side elevation view of the ablation device of FIG. 11A.

FIG. 11C is a cross-sectional end view of the ablation device of FIG. 11A.

FIG. 12A is a perspective view of an eighth embodiment of an ablation device utilizing principles of the present invention.

FIG. 12B is a cross-sectional side elevation view of the ablation device of FIG. 12A.

FIG. 15A is a cross-sectional side elevation view of an eleventh embodiment.

FIG. 15B is a cross-sectional end view of the eleventh embodiment taken along the plane designated 15B—15B in FIG. 15A.

FIGS. 16A–16D are a series of drawings illustrating use of the eleventh embodiment.

FIG. 18 is a series of plots graphically illustrating the impact of electrode spacing on the ablation device output at the body tissue/fluid load.

DETAILED DESCRIPTION

Figure 3:
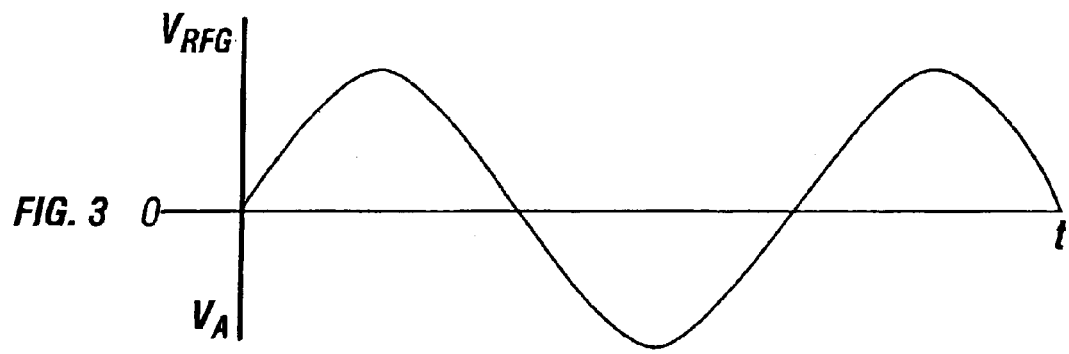
FIG. 3 is a graphical representation of voltage output from an RF generator output over time.

Several embodiments of ablation systems useful for practicing a voltage threshold ablation method utilizing principles of the present invention are shown in the drawings. Generally speaking, each of these systems utilizes a switching means that prevents current flow into body tissue until the voltage across the switching means reaches a predetermined threshold potential. By preventing current flow into tissue until a high threshold voltage is reached, the invention minimizes collateral tissue damage that can occur when a large amount of current is applied to the tissue. The switching means may take a variety of forms, including but not limited to an encapsulated or circulated volume of argon or other fluid/gas that will only conduct ablation energy from an intermediate electrode to the ablation electrodes once it has been transformed to a plasma by being raised to a threshold voltage.

The embodiments described herein utilize a spark gap switch for preventing conduction of energy to the tissue until the voltage potential applied by the RF generator reaches a threshold voltage. In a preferred form of the apparatus, the spark gap switch includes a volume of fluid/gas to conduct ablation energy across the spark gap, typically from an intermediate electrode to an ablation electrode. The fluid/gas used for this purpose is one that will not conduct until it has been transformed to conductive plasma by having been raised to a threshold voltage. The threshold voltage of the fluid/gas will vary with variations in a number of conditions, including fluid/gas pressure, distance across the spark gap (e.g. between an electrode on one side of the spark gap and an electrode on the other side of the spark gap), and with the rate at which the fluid/gas flows within the spark gap—if flowing fluid/gas is used. As will be seen in some of the embodiments, the threshold voltage may be adjusted in some embodiments by changing any or all of these conditions.

A first embodiment of an ablation device 10 utilizing principles of the present invention is shown in FIGS. 1–2. Device 10 includes a housing 12 formed of an insulating material such as glass, ceramic, siliciumoxid, PTFE or other material having a high melting temperature. At the distal end 13 of the housing 12 is a sealed reservoir 20. An internal electrode 22 is disposed within the sealed reservoir 20. Electrode 22 is electrically coupled to a conductor 24 that extends through the housing body. Conductor 24 is coupled to an RF generator 28 which may be a conventional RF generator used for medical ablation, such as the Model Force 2 RF Generator manufactured by Valley Lab. A return electrode 30 is disposed on the exterior surface of the housing 12 and is also electrically coupled to RF generator 28.

A plurality of ablation electrodes 32a–32e are located on the distal end of the housing 12. Ablation electrodes 32a–32e may be formed of tungsten or any conductive material which performs well when exposed to high temperatures. In an alternative embodiment, there may be only one ablation electrode, or a different electrode configuration.

FIGS. 5A through 5D illustrate the method of using the embodiment of FIG. 1. Referring to FIGS. 5A, prior to use the reservoir 20 is filled with a fluid or gas. Preferably, an inert gas such as argon gas or a similar gas such as Neon, Xenon, or Helium is utilized to prevent corrosion of the electrodes, although other fluids/gases could be utilized so long as the electrodes and other components were appropriately protected from corrosion. For convenience only, the embodiments utilizing such a fluid/gas will be described as being used with the preferred gas, which is argon.

It should be noted that while the method of FIGS. 5A–5D is most preferably practiced with a sealed volume of gas within the reservoir 20, a circulating flow of gas using a system of lumens in the housing body may alternatively be used. A system utilizing a circulating gas flow is described in connection with FIGS. 15A–15B.

The distal end of the device 10 is placed against body tissue to be ablated, such that some of the electrodes 32a, 32b contact the tissue T. In most instances, others of the electrodes 32c are disposed within body fluids B. The RF generator 28 is powered on and gradually builds-up the voltage potential between electrode 22 and electrodes 32a–32c.

Despite the voltage potential between the internal electrode 22 and ablation electrodes 32a–c, there initially is no conduction of current between them. This is because the argon gas will not conduct current when it is in a gas phase. In order to conduct, high voltages must be applied through the argon gas to create a spark to ionize the argon and bring it into the conductive plasma phase. Later in this description these voltages may also be referred to as "initiating voltages" since they are the voltages at which conduction is initiated.

The threshold voltage at which the argon will begin to immediately conduct is dependent on the pressure of the argon gas and the distance between electrode 22 and surface electrodes 32a–32c.

Assume P1 is the initial pressure of the argon gas within reservoir 20. If, at pressure P1, a voltage of V1 is required to ignite plasma within the argon gas, then a voltage of V>V1 must be applied to electrode 22 to ignite the plasma and to thus begin conduction of current from electrode 22 to ablation electrodes 32a–32c.

Thus, no conduction to electrodes 32a–32c (and thus into the tissue) will occur until the voltage potential between electrode 22 and ablation electrodes 32a–32c reaches voltage V. Since no current flows into the tissue during the time when the RF generator is increasing its output voltage towards the voltage threshold, there is minimal resistive heating of the electrodes 32a–32c and body tissue. Thus, this method relies on the threshold voltage of the argon (i.e. the voltage at which a plasma is ignited) to prevent overheating of the ablation electrodes 32a, 32b and to thus prevent tissue from sticking to the electrodes.

The voltage applied by the RF generator to electrode 22 cycles between +V and −V throughout the ablation procedure. However, as the process continues, the temperature within the reservoir begins to increase, causing the pressure of the argon to likewise increase. As the gas pressure increases, the voltage needed to ignite the plasma also increases. Eventually, increases in temperature and thus pressure will cause the voltage threshold needed to ignite the plasma to increase above V. When this occurs, flow of current to the ablation electrodes will stop until the argon temperature and pressure decrease to a point where the voltage required for plasma ignition is at or below V. Initial gas pressure P1 and the voltage V are thus selected such that current flow will terminate when the electrode temperature is reaching a point at which tissue will stick to the electrodes.

Figure 4A:
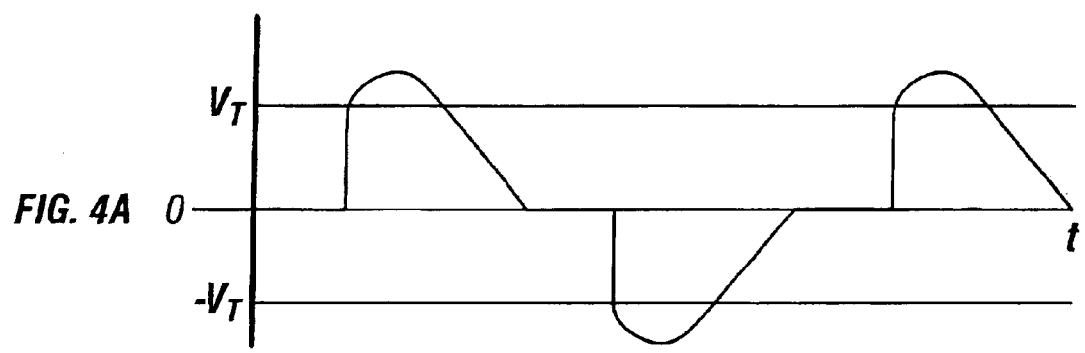
FIG. 4A is a graphical representation of voltage potential across a body tissue load, from an ablation device utilizing voltage threshold ablation techniques as described herein.

The effect of utilizing a minimum voltage limit on the potential applied to the tissue is illustrated graphically in FIGS. 3 and 4A. FIG. 3 shows RF generator voltage output $V_{RF}$ over time, and FIG. 4A shows the ablation potential $V_A$ between internal electrode 22 and body tissue. As can be seen, $V_A$ remains at 0V until the RF generator output $V_{RF}$ reaches the device's voltage threshold $V_T$, at which time $V_A$ rises immediately to the threshold voltage level. Ablation voltage $V_A$ remains approximately equivalent to the RF generator output until the RF generator output reaches 0V. $V_A$ remains at 0V until the negative half-cycle of the RF generator output falls below $(-V_T)$, at which time the potential between electrode 22 and the tissue drops immediately to $(-V_T)$, and so on. Because there is no conduction to the tissue during the time that the RF generator output is approaching the voltage threshold, there is little conduction to the tissue during low voltage (and high current) phases of the RF generator output. This minimizes collateral tissue damages that would otherwise be caused by resistive heating.

Figure 4B:
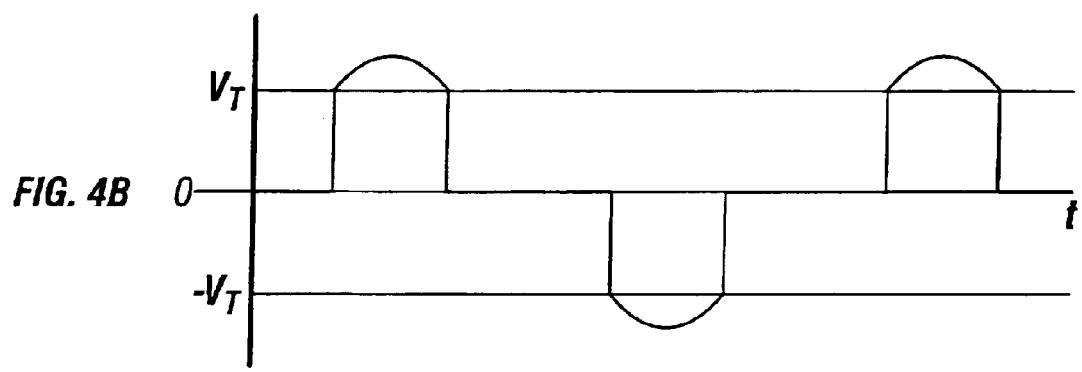
FIG. 4B is a graphical representation of voltage potential across a body tissue load, from an ablation device utilizing voltage threshold ablation techniques as described herein and further utilizing techniques described herein for decreasing the slope of the trailing edge of the waveform.

It is further desirable to eliminate the sinusoidal trailing end of the waveform as an additional means of preventing application of low voltage/high current to the tissue and thus eliminating collateral tissue damage. Additional features are described below with respect FIGS. 14A–18. These additional features allow this trailing edge to be clipped and thus produce a waveform measured at the electrode/tissue interface approximating that shown in FIG. 4B.

Another phenomenon occurs between the electrodes 32a–32c and the tissue, which further helps to keep the electrodes sufficiently cool as to avoid sticking. This phenomenon is best described with reference to FIGS. 5A through 5D. As mentioned, in most cases some of the electrodes such as electrode 32c will be in contact with body fluid while others (e.g. 32a–b) are in contact with tissue. Since the impedance of body fluid F is low relative to the impedance of tissue T, current will initially flow through the plasma to electrode 32c and into the body fluid to return electrode 30, rather than flowing to the electrodes 32, 32b that contact tissue T.

Resistive heating of electrode 32c causes the temperature of body fluid F to increase. Eventually, the body fluid F reaches a boiling phase and a resistive gas/steam bubble G will form at electrode 32c. Steam bubble G increases the distance between electrode 22 and body fluid F from distance D1 to distance D2 as shown in FIG. 5B. The voltage at which the argon will sustain conductive plasma is dependent in part on the distance between electrode 22 and the body fluid F. If the potential between electrode 22 and body fluid F is sufficient to maintain a plasma in the argon even after the bubble G has expanded, energy will continue to conduct through the argon to electrode 32c, and sparking will occur through bubble G between electrode 32c and the body fluid F.

Continued heating of body fluid F causes gas/steam bubble G to further expand. Eventually the size of bubble G is large enough to increase the distance between electrode 22 and fluid F to be great enough that the potential between them is insufficient to sustain the plasma and to continue the sparking across the bubble G. Thus, the plasma between electrodes 22 and 32c dies, causing sparking to discontinue and causing the current to divert to electrodes 32a, 32b into body tissue T, causing ablation to occur. See FIG. 5C. A gas/steam insulating layer L will form in the region surrounding the electrodes 32a, 32b. By this time, gas/steam bubble G around electrode 32c may have dissipated, and the high resistance of the layer L will cause the current to divert once again into body fluid F via electrode 32c rather than through electrodes 32a, 32b. This process may repeat many times during the ablation procedure.

A second embodiment of an ablation device 110 is shown in FIGS. 6A and 6B. The second embodiment operates in a manner similar to the method described with respect to the first embodiment, but it includes structural features that allow the threshold voltage of the argon to be pre-selected. Certain body tissues require higher voltages in order for ablation to be achieved. This embodiment allows the user to select the desired ablation voltage and to have the system prevent current conduction until the pre-selected voltages are reached. Thus, there is no passage of current to the tissue until the desired ablation voltage is reached, and so there is no unnecessary resistive tissue heating during the rise-time of the voltage.

As discussed previously, the voltage threshold of the argon varies with the argon pressure in reservoir 120 and with the distance d across the spark gap, i.e. the distance extending between electrode 122 and ablation electrodes 132a–c. The second embodiment allows the argon pressure and/or the distance d to be varied so as to allow the voltage threshold of the argon to be pre-selected to be equivalent to the desired ablation voltage for the target tissue. In other words, if a treatment voltage of 200V is desired, the user can configure the second embodiment such that that voltage will be the threshold voltage for the argon. Treatment voltages in the range of 50V to 10,000V, and most preferably 200V–500V, may be utilized.

Referring to FIG. 6A, device 110 includes a housing 112 formed of an insulating material such as glass, ceramic, siliciumoxid, PTFE or other high melting temperature material. A reservoir 120 housing a volume of argon gas is located in the housing's distal tip. A plunger 121 is disposed within the housing 112 and includes a wall 123. The plunger is moveable to move the wall proximally and distally between positions 121A and 121B to change the volume of reservoir 120. Plunger wall 123 is sealable against the interior wall of housing 112 so as to prevent leakage of the argon gas.

An elongate rod 126 extends through an opening (not shown) in plunger wall 123 and is fixed to the wall 123 such that the rod and wall can move as a single component. Rod 126 extends to the proximal end of the device 110 and thus may serve as the handle used to move the plunger 121 during use.

Internal electrode 122 is positioned within the reservoir 120 and is mounted to the distal end of rod 126 such that movement of the plunger 121 results in corresponding movement of the electrode 122. Electrode 122 is electrically coupled to a conductor 124 that extends through rod 126 and that is electrically coupled to RF generator 128. Rod 126 preferably serves as the insulator for conductor 124 and as such should be formed of an insulating material.

A return electrode 130 is disposed on the exterior surface of the housing 112 and is also electrically coupled to RF generator 128. A plurality of ablation electrodes 132a, 132b etc. are positioned on the distal end of the housing 112.

Operation of the embodiment of FIGS. 6A–6B is similar to that described with respect to FIGS. 5A–5B, and so most of that description will not be repeated. Operation differs in that use of the second embodiment includes the preliminary step of moving rod 126 proximally or distally to place plunger wall 123 and electrode 122 into positions that will yield a desired voltage threshold for the argon gas. Moving the plunger in a distal direction (towards the electrodes 132*a–c*) will decrease the volume of the reservoir and accordingly will increase the pressure of the argon within the reservoir and vice versa. Increases in argon pressure result in increased voltage threshold, while decreases in argon pressure result in decreased voltage threshold.

Moving the plunger 126 will also increase or decrease the distance d between electrode 122 and electrodes 132*a–c*. Increases in the distance d increase the voltage threshold and vice versa.

The rod 126 preferably is marked with calibrations showing the voltage threshold that would be established using each position of the plunger. This will allow the user to move the rod 126 inwardly (to increase argon pressure but decrease distance d) or outwardly (to decrease argon pressure but increase distance d) to a position that will give a threshold voltage corresponding to the voltage desired to be applied to the tissue to be ablated. Because the argon will not ignite into a plasma until the threshold voltage is reached, current will not flow to the electrodes 132*a*, 132*b* etc. until the pre-selected threshold voltage is reached. Thus, there is no unnecessary resistive tissue heating during the rise-time of the voltage.

Alternatively, the FIG. 6A embodiment may be configured such that plunger 121 and rod 126 may be moved independently of one another, so that argon pressure and the distance d may be adjusted independently of one another. Thus, if an increase in voltage threshold is desired, plunger wall 123 may be moved distally to increase argon pressure, or rod 126 may be moved proximally to increase the separation distance between electrode 122 and 132*a–c*. Likewise, a decrease in voltage threshold may be achieved by moving plunger wall 123 proximally to decrease argon pressure, or by moving rod 126 distally to decrease the separation distance d. If such a modification to the FIG. 6A was employed, a separate actuator would be attached to plunger 121 to allow the user to move the wall 123, and the plunger 126 would be slidable relative to the opening in the wall 123 through which it extends.

During use of the embodiment of FIGS. 6A and 6B, it may be desirable to maintain a constant argon pressure despite increases in temperature. As discussed in connection with the method of FIGS. 5A–5D, eventual increases in temperature and pressure cause the voltage needed to ignite the argon to increase above the voltage being applied by the RF generator, resulting in termination of conduction of the electrodes. In the FIG. 6A embodiment, the pressure of the argon can be maintained despite increases in temperature by withdrawing plunger 121 gradually as the argon temperature increases. By maintaining the argon pressure, the threshold voltage of the argon is also maintained, and so argon plasma will continue to conduct current to the electrodes 132*a* 132*b* etc. Similarly, the position of electrode 122 may be changed during use so as to maintain a constant voltage threshold despite argon temperature increases.

FIGS. 7A and 7B show an alternative embodiment of an ablation device 210 that is similar to the device of FIGS. 6A and 6B. In this embodiment, argon is sealed within reservoir 220 by a wall 217. Rather than utilizing a plunger (such as plunger 121 in FIG. 6A) to change the volume of reservoir 220, the FIGS. 7A–7B embodiment utilizes bellows 221 formed into the sidewalls of housing 212 and a pullwire 226 (which may double as the insulation for conductor 224) extending through internal electrode 222 and anchored to the distal end of the housing 212. Pulling the pullwire 226 collapses the bellows into a contracted position as shown in FIG. 7A and increases the pressure of the argon within the reservoir 220. Advancing the pullwire 226 expands the bellows as shown in FIG. 7B, thereby decreasing the pressure of the argon. The pullwire and bellows may be used to pre-select the threshold voltage, since (for a given temperature) increasing the argon pressure increases the threshold voltage of the argon and vice versa. Once the threshold voltage has been pre-set, operation is similar to that of the previous embodiments. It should be noted that in the third embodiment, the distance between electrode 222 and ablation electrodes 232*a–c* remains fixed, although the device may be modified to allow the user to adjust this distance and to provide an additional mechanism for adjusting the voltage threshold of the device.

An added advantage of the embodiment of FIG. 7A is that the device may be configured to permit the bellows 221 to expand in response to increased argon pressure within the reservoir. This will maintain the argon pressure, and thus the threshold voltage of the argon, at a fairly constant level despite temperature increases within reservoir 220. Thus, argon plasma will continue to conduct current to the electrodes 132*a* 132*b* etc and ablation may be continued, as it will be a longer period of time until the threshold voltage of the argon exceeds the voltage applied by the RF generator.

An expanding volume embodiment, such as the embodiment of FIG. 7, may be configured such that the volume expands but such that the spacing between the internal electrode and the ablation electrode remains constant even during expansion of the volume. This allows the system to increase in volume in response to pressure increases, but permits conduction between the internal electrode and the ablation electrode for a longer period of time.

FIGS. 8A through 13B are a series of embodiments that also utilize argon, but that maintain a fixed reservoir volume for the argon. In each of these embodiments, current is conducted from an internal electrode within the argon reservoir to external ablation electrodes once the voltage of the internal electrode reaches the threshold voltage of the argon gas.

Figure 8B:
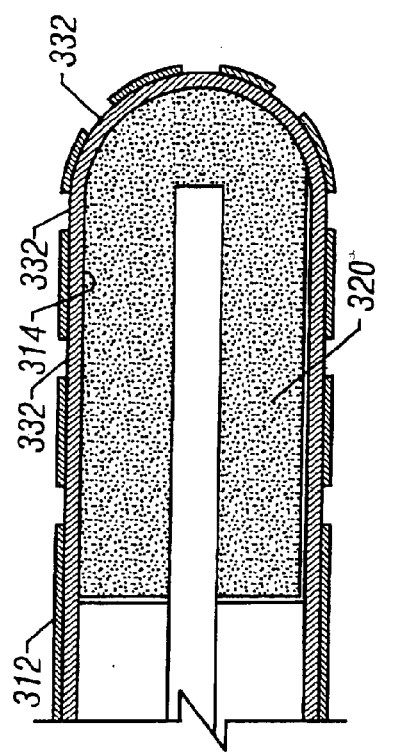
FIG. 8B is a cross-sectional side elevation view of the ablation device of FIG. 8A.
Figure 8A:
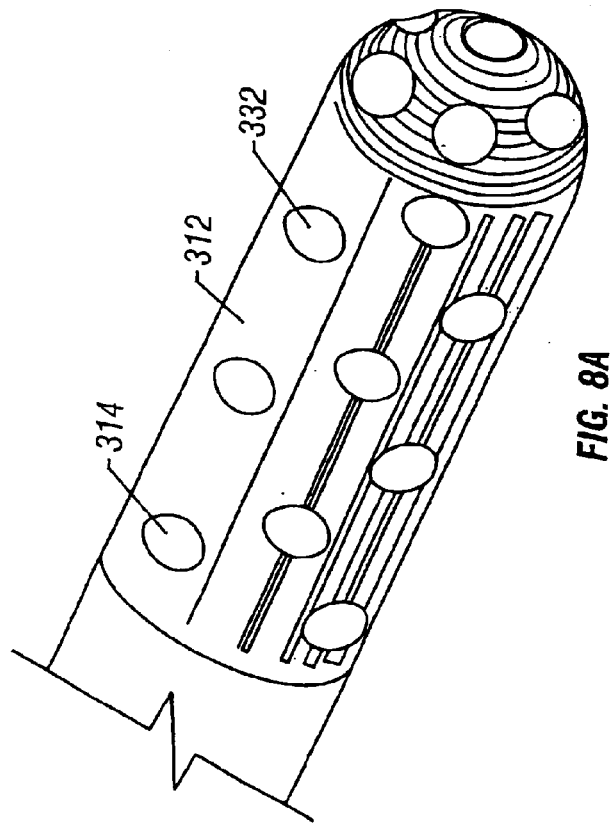
FIG. 8A is a perspective view of a fourth embodiment of an ablation device utilizing principles of the present invention.
Figure 9B:
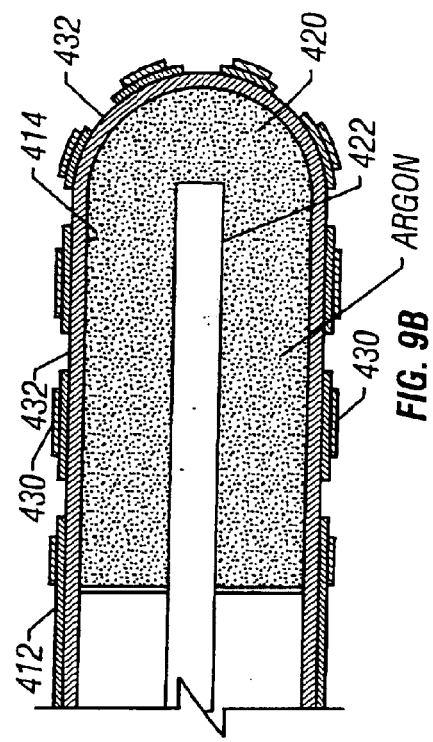
FIG. 9B is a cross-sectional side elevation view of the ablation device of FIG. 9A.
Figure 9A:
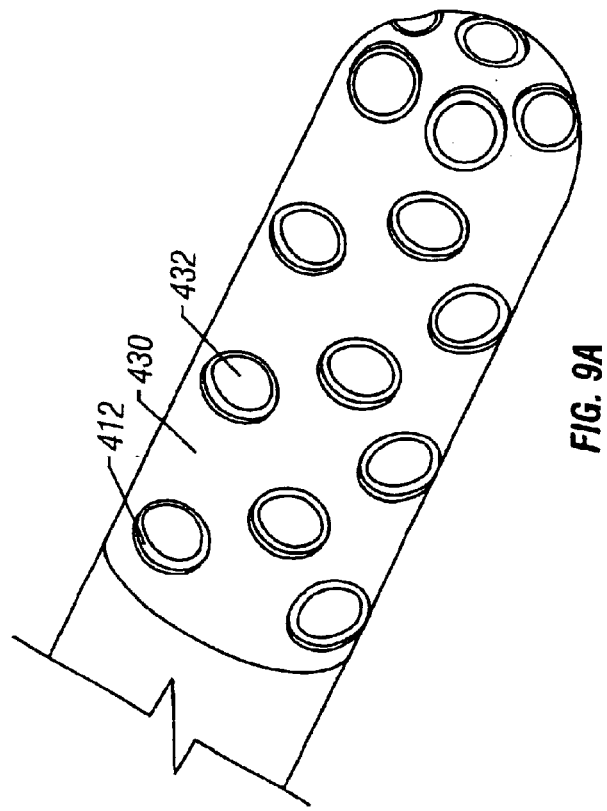
FIG. 9A is a perspective view of a fifth embodiment of an ablation device utilizing principles of the present invention.

Referring to FIGS. 8A and 8B, the fourth embodiment of an ablation device utilizes a housing 312 formed of insulating material, overlaying a conductive member 314. Housing 312 includes exposed regions 332 in which the insulating material is removed to expose the underlying conductive member 314. An enclosed reservoir 320 within the housing 212 contains argon gas, and an RF electrode member 322 is positioned within the reservoir. A return electrode (not shown) is attached to the patient. The fourth embodiment operates in the manner described with respect to FIGS. 5A–5D, except that the current returns to the RF generator via the return electrode on the patient's body rather than via one on the device itself The fifth embodiment shown in FIGS. 9A and 9B is similar in structure and operation to the fourth embodiment. A conductive member 414 is positioned beneath insulated housing 412, and openings in the housing expose electrode regions 432 of the conductive member 414. The fifth embodiment differs from the fourth embodiment in that it is a bipolar device having a return electrode 430 formed over the insulated housing 412. Return electrode 430 is coupled to the RF generator and is cutaway in the same regions in which housing 412 is cutaway; so as to expose the underlying conductor.

Internal electrode 422 is disposed within argon gas reservoir 420. During use, electrode regions 432 are placed into contact with body tissue to be ablated. The RF generator is switched on and begins to build the voltage of electrode 422 relative to ablation electrode regions 432. As with the previous embodiments, conduction of ablation energy from electrode 422 to electrode regions 432 will only begin once electrode 422 reaches the voltage threshold at which the argon in reservoir 420 ignites to form a plasma. Current passes through the tissue undergoing ablation and to the return electrode 430 on the device exterior.

Figure 10:
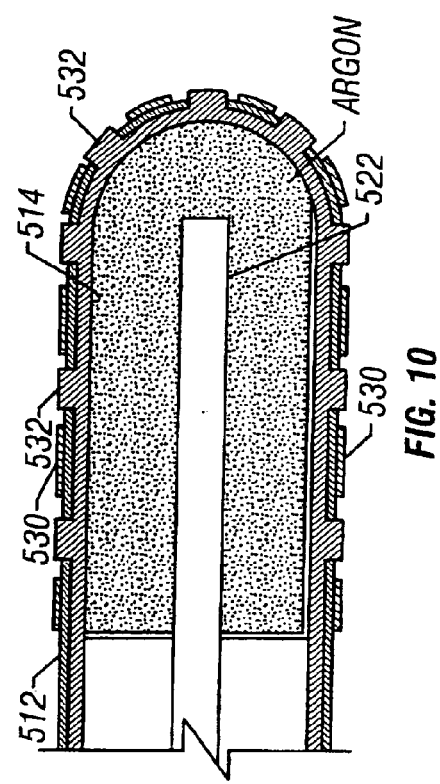
FIG. 10 is a cross-sectional side elevation view of a sixth ablation device utilizing principles of the present invention.

The sixth embodiment shown in FIG. 10 is similar in structure and operation to the fifth embodiment, and thus includes a conductive member 514, an insulated housing 512 over the conductive member 512 and having openings to expose regions 532 of the conductive member. A return electrode 530 is formed over the housing 512, and an internal electrode 522 is positioned within a reservoir 520 containing a fixed volume of argon. The sixth embodiment differs from the fifth embodiment in that the exposed regions 532 of the conductive member 514 protrude through the housing 512 as shown. This is beneficial in that it improves contact between the exposed regions 532 and the target body tissue.

Figure 11A:
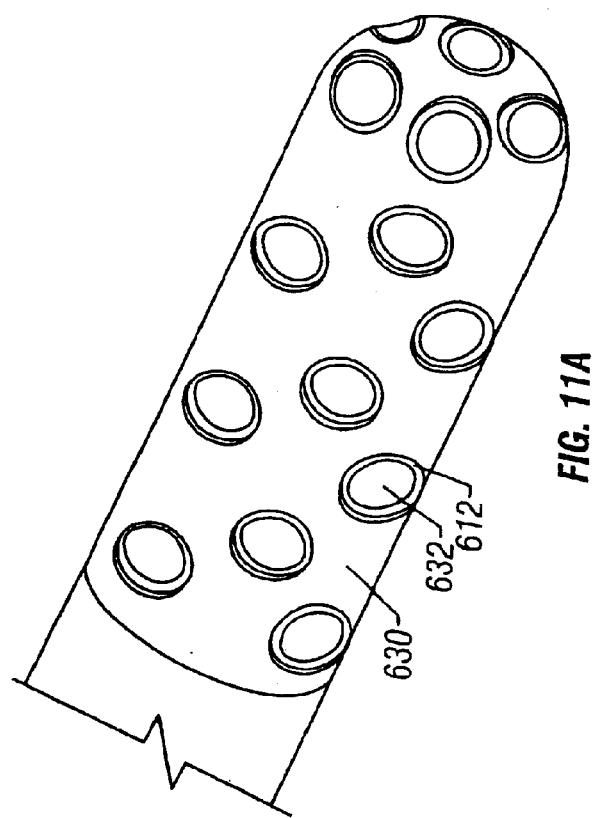
FIG. 11A is a perspective view of a seventh embodiment of an ablation device utilizing principles of the present invention.

A seventh embodiment is shown in FIGS. 11A through 11C. As with the sixth embodiment, this embodiment includes an insulated housing 612 formed over a conductive member 614, and openings in the insulated housing 612 to expose elevated electrode regions 632 of the conductive member 614. A return electrode 630 is formed over the housing 612. An internal electrode 622 is positioned within a reservoir 620 containing a fixed volume of argon.

The seventh embodiment differs from the sixth embodiment in that there is an annular gap 633 between the insulated housing 614 and the elevated regions 632 of the conductive member 614. Annular gap 633 is fluidly coupled to a source of suction and/or to an irrigation supply. During use, suction may be applied via gap 633 to remove ablation byproducts (e.g. tissue and other debris) and/or to improve electrode contact by drawing tissue into the annular regions between electrode regions 632 and ground electrode 630. An irrigation gas or fluid may also be introduced via gap 633 during use so as to flush ablation byproducts from the device and to cool the ablation tip and the body tissue. Conductive or non-conductive fluid may be utilized periodically during the ablation procedure to flush the system.

Annular gap 633 may also be used to deliver argon gas into contact with the electrodes 632. When the voltage of the electrode regions 632 reaches the threshold of argon delivered through the gap 633, the resulting argon plasma will conduct from electrode regions 632 to the ground electrode 630, causing lateral sparking between the electrodes 632, 630. The resulting sparks create an "electrical file" which cuts the surrounding body tissue An eighth embodiment of an ablation device is shown in FIGS. 12B and 12C. This device 710 is similar to the device of the fifth embodiment, FIGS. 9A and 9B, in a number of ways. In particular, device 710 includes a conductive member 714 positioned beneath insulated housing 712, and openings in the housing which expose electrode regions 732 of the conductive member 714. A return electrode 730 is formed over the insulated housing 712. Internal electrode 722 is disposed within an argon gas reservoir 720 having a fixed volume.

The eighth embodiment additionally includes a pair of telescoping tubular jackets 740, 742. Inner jacket 740 has a lower insulating surface 744 and an upper conductive surface 746 that serves as a second return electrode. Inner jacket 740 is longitudinally slidable between proximal position 740A and distal position 740B.

Outer jacket 742 is formed of insulating material and is slidable longitudinally between position 742A and distal position 742B.

A first annular gap 748 is formed beneath inner jacket 740 and a second annular gap 750 is formed between the inner and outer jackets 740, 742. These gaps may be used to deliver suction or irrigation to the ablation site to remove ablation byproducts.

The eighth embodiment may be used in a variety of ways. As a first example, jackets 740, 742 may be moved distally to expose less than all of tip electrode assembly (i.e. the region at which the conductive regions 732 are located). This allows the user to expose only enough of the conductive regions 732 as is needed to cover the area to be ablated within the body. Secondly, in the event bleeding occurs at the ablation site, return electrode surface 730 may be used as a large surface area coagulation electrode, with return electrode surface 746 serving as the return electrode, so as to coagulate the tissue and to thus stop the bleeding. Outer jacket 742 may be moved proximally or distally to increase or decrease the surface area of electrode 746. Moving it proximally has the effect of reducing the energy density at the return electrode 746, allowing power to be increased to carry out the coagulation without increasing thermal treatment effects at return electrode 746.

Alternatively, in the event coagulation and/or is needed, electrode 730 may be used for surface coagulation in combination with a return patch placed into contact with the patient.

Figure 13B:
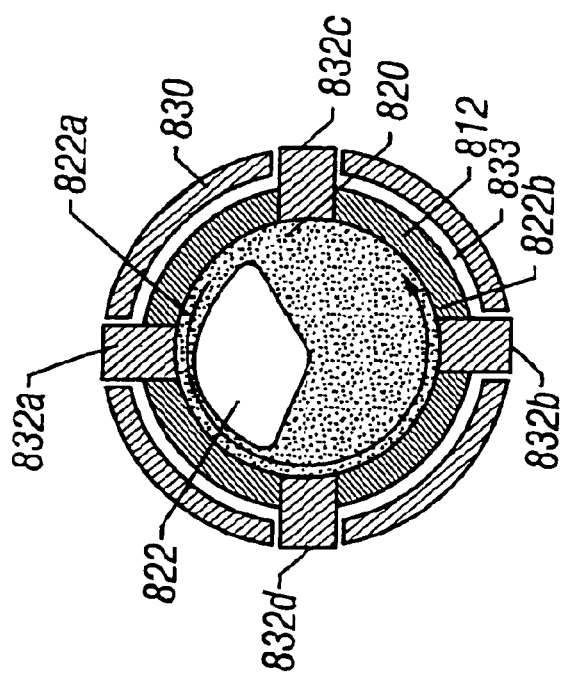
FIG. 13B is a cross-sectional end view of the ablation device of FIG. 13A, taken along the plane designated 13B—13B in FIG. 13A.
Figure 13A:
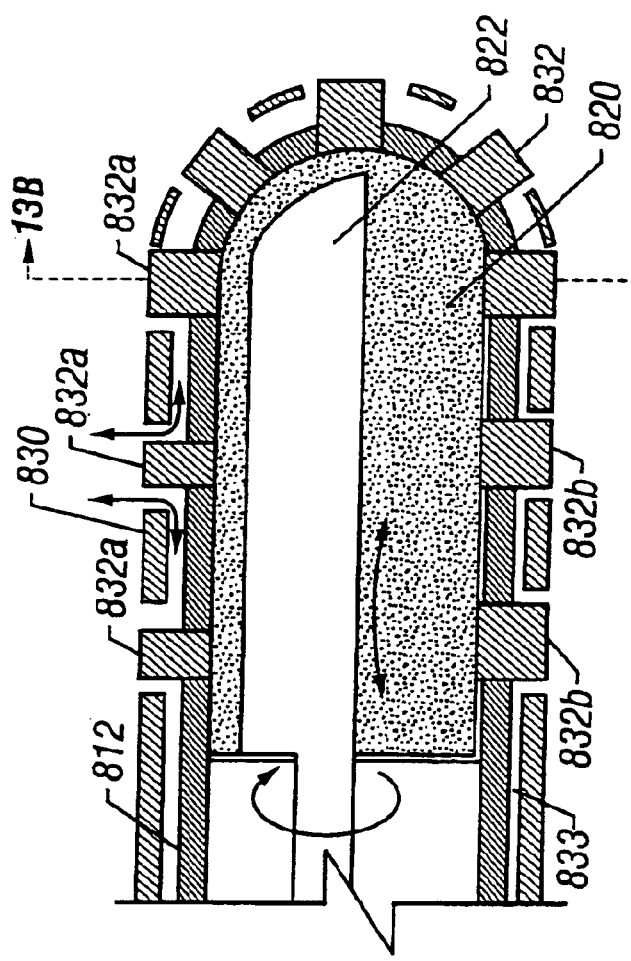
FIG. 13A is a cross-sectional side elevation view of a ninth embodiment of an ablation device utilizing principles of the present invention.

FIGS. 13A–13B show a ninth embodiment of an ablation device utilizing principles of the present invention. The ninth embodiment includes an insulated housing 812 having an argon gas reservoir 820 of fixed volume. A plurality of ablation electrodes 832 are embedded in the walls of the housing 812 such that they are exposed to the argon in reservoir 832 and exposed on the exterior of the device for contact with body tissue. A return electrode 830 is formed over the housing 812, but includes openings through which the electrodes 832 extend. An annular gap 833 lies between return electrode 830 and housing 812. As with previous embodiments, suction and/or irrigation may be provided through the gap 833. Additionally, argon gas may be introduced through the annular gap 833 and into contact with the electrodes 832 and body tissue so as to allow argon gas ablation to be performed.

An internal electrode 822 is positioned within reservoir 820. Electrode 822 is asymmetrical in shape, having a curved surface 822a forming an arc of a circle and a pair of straight surfaces 822b forming radii of the circle. As a result of its shape, the curved surface of the electrode 820 is always closer to the electrodes 832 than the straight surfaces. Naturally, other shapes that achieve this effect may alternatively be utilized.

Electrode 822 is rotatable about a longitudinal axis and can also be moved longitudinally as indicated by arrows in FIGS. 13A and 13B. Rotation and longitudinal movement can be carried out simultaneously or separately. This allows the user to selectively position the surface 822a in proximity to a select group of the electrodes 832. For example, referring to FIGS. 13A and 13B, when electrode 822 is positioned as shown, curved surface 822a is near electrodes 832a, whereas no part of the electrode 822 is close to the other groups of electrodes 832b–d.

As discussed earlier, the voltage threshold required to cause conduction between internal electrode 822 and ablation electrodes 832 will decrease with a decrease in distance between the electrodes. Thus, there will be a lower threshold voltage between electrode 822 and the ablation electrodes (e.g. electrode 832*a*) adjacent to surface 822*a* than there is between the electrode 822 and ablation electrodes that are farther away (e.g. electrodes 832*b–d*). The dimensions of the electrode 822 and the voltage applied to electrode 822 are such that a plasma can only be established between the surface 822*a* and the electrodes it is close to. Thus, for example, when surface 822*a* is adjacent to electrodes 832*a* as shown in the drawings, the voltage threshold between the electrodes 822*a* and 832*a* is low enough that the voltage applied to electrode 822 will cause plasma conduction to electrodes 832*a*. However, the threshold between electrode 822 and the other electrodes 832*b–d* will remain above the voltage applied to electrode 822, and so there will be no conduction to those electrodes.

This embodiment thus allows the user to selectively ablate regions of tissue by positioning the electrode surface 822*a* close to electrodes in contact with the regions at which ablation is desired.

Figure 14B:
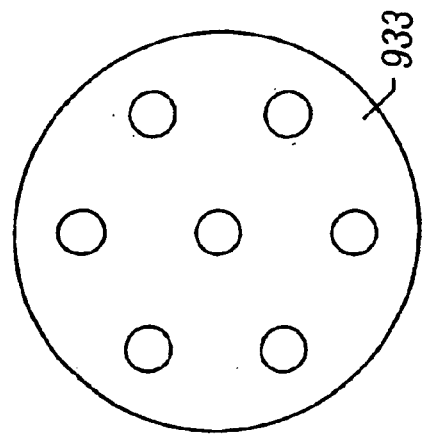
FIG. 14B is a front end view of the grid utilized in the embodiment of FIG. 14A.
Figure 14A:
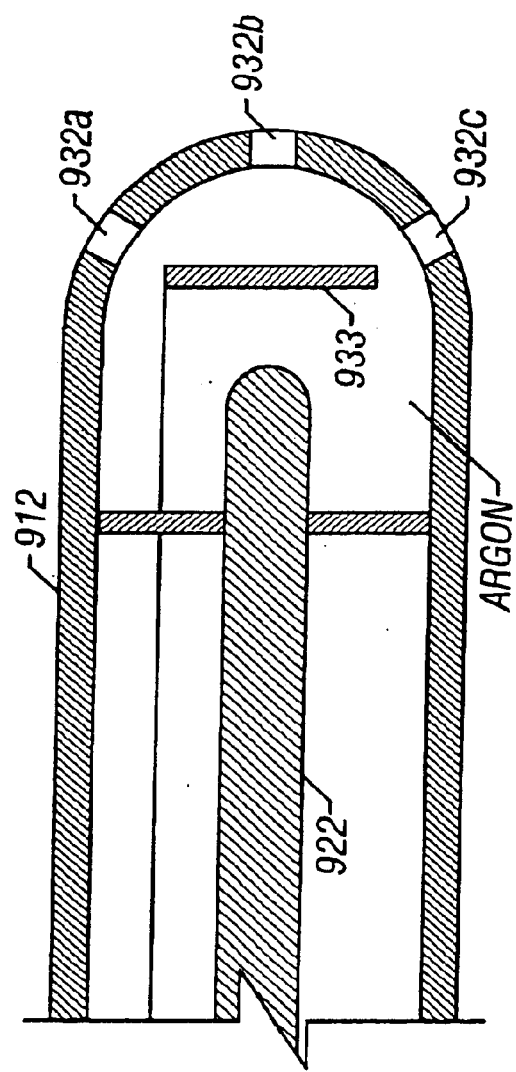
FIG. 14A is a cross-sectional side elevation view of a tenth embodiment of an ablation device utilizing principles of the present invention.

FIG. 14A shows a tenth embodiment of an ablation device utilizing voltage threshold principles. The tenth embodiment includes a housing 912 having a sealed distal end containing argon. Ablation electrodes 932*a–c* are positioned on the exterior of the housing 912. An internal electrode 922 is disposed in the sealed distal end. Positioned between the internal electrode 922 and the electrodes 932*a–c* is a conductive grid 933.

When electrode 922 is energized, there will be no conduction from electrode 922 to electrodes 932*a–c* until the potential between electrode 922 and the body tissue/fluid in contact with electrodes 932*a–c* reaches an initiating threshold voltage at which the argon gas will form a conductive plasma. The exact initiating threshold voltage is dependent on the argon pressure, its flowrate (if it is circulating within the device), and the distance between electrode 922 and the tissue/body fluid in contact with the ablation electrodes 932*a–c*.

Because the RF generator voltage output varies sinusoidally with time, there are phases along the RF generator output cycle at which the RF generator voltage will drop below the voltage threshold. However, once the plasma has been ignited, the presence of energized plasma ions in the argon will maintain conduction even after the potential between electrode 922 and the body fluid/tissue has been fallen below the initiating threshold voltage. In other words, there is a threshold sustaining voltage that is below the initiating threshold voltage, but that will sustain plasma conduction.

In the embodiment of FIG. 14A, the grid 933 is spaced from the electrodes 932*a–c* by a distance at which the corresponding plasma ignition threshold is a suitable ablation voltage for the application to which the ablation device is to be used. Moreover, the electrode 922 is positioned such that once the plasma is ignited, grid 933 may be deactivated and electrode 922 will continue to maintain a potential equal to or above the sustaining voltage for the plasma. Thus, during use, both grid 933 and electrode 922 are initially activated for plasma formation. Once the potential between grid 933 and body tissue/fluid reaches the threshold voltage and the plasma ignites, grid 933 will be deactivated. Because ions are present in the plasma at this point, conduction will continue at the sustaining threshold voltage provided by electrode 922.

The ability of ionized gas molecules in the argon to sustain conduction even after the potential applied to the internal electrode has fallen below the initiating threshold voltage can be undesirable. As discussed, an important aspect of voltage threshold ablation is that it allows for high voltage/low current ablation. Using the embodiments described herein, a voltage considered desirable for the application is selected as the threshold voltage. Because the ablation electrodes are prevented from conducting when the voltage delivered by the RF generator is below the threshold voltage, there is no conduction to the ablation electrode during the rise time from 0 V to the voltage threshold. Thus, there is no resistive heating of the tissue during the period in which the RF generator voltage is rising towards the threshold voltage.

Under ideal circumstances, conduction would discontinue during the periods in which the RF generator voltage is below the threshold. However, since ionized gas remains in the argon reservoir, conduction can continue at voltages below the threshold voltage. Referring to FIG. 4A, this results in the sloping trailing edge of the ablation voltage waveform, which approximates the trailing portion of the sinusoidal waveform produced by the RF generator (FIG. 3). This low-voltage conduction to the tissue causes resistive heating of the tissue when only high voltage ablation is desired.

The grid embodiment of FIG. 14A may be used to counter the effect of continued conduction so as to minimize collateral damage resulting from tissue heating. During use of the grid embodiment, the trailing edge of the ablation voltage waveform is straightened by reversing the polarity of grid electrode 933 after the RF generator has reached its peak voltage. This results in formation of a reverse field within the argon, which prevents the plasma flow of ions within the argon gas and that thus greatly reduces conduction. This steepens the slop of the trailing edge of the ablation potential waveform, causing a more rapid drop towards 0 V, such that it approximates the waveform shown in FIG. 4B.

FIGS. 15A and 15B show an eleventh embodiment utilizing principles of the present invention. As with the tenth embodiment, the eleventh embodiment is advantageous in that it utilizes a mechanism for steepening the trailing edge of the ablation waveform, thus minimizing conduction during periods when the voltage is below the threshold voltage. In the eleventh embodiment, this is accomplished by circulating the argon gas through the device so as to continuously flush a portion of the ionized gas molecules away from the ablation electrodes.

The eleventh embodiment includes a housing 1012 having an ablation electrodes 1032. An internal electrode 1022 is positioned within the housing 1012 and is preferably formed of conductive hypotube having insulation 1033 formed over all but the distal-most region. A fluid lumen 1035 is formed in the hypotube and provides the conduit through which argon flows into the distal region of housing 1012. Flowing argon exits the housing through the lumen in the housing 1012, as indicated by arrows in FIG. 15A. A pump 1031 drives the argon flow through the housing.

Figure 15C:
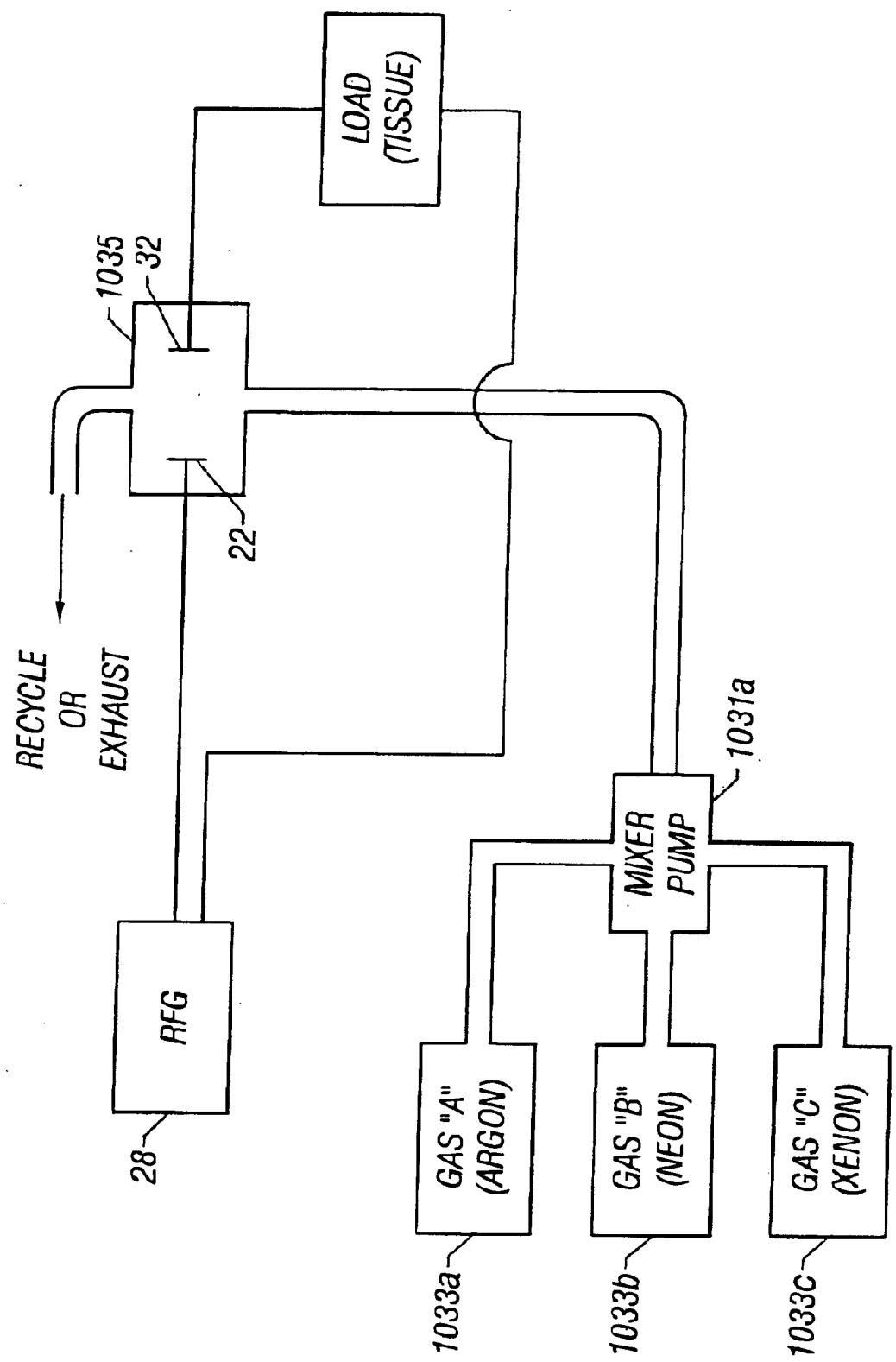
FIG. 15C is a schematic illustration of a variation of the eleventh embodiment, in which the mixture of gases used in the reservoir may be adjusted so as to change the threshold voltage.
Figures 16C, 16D:
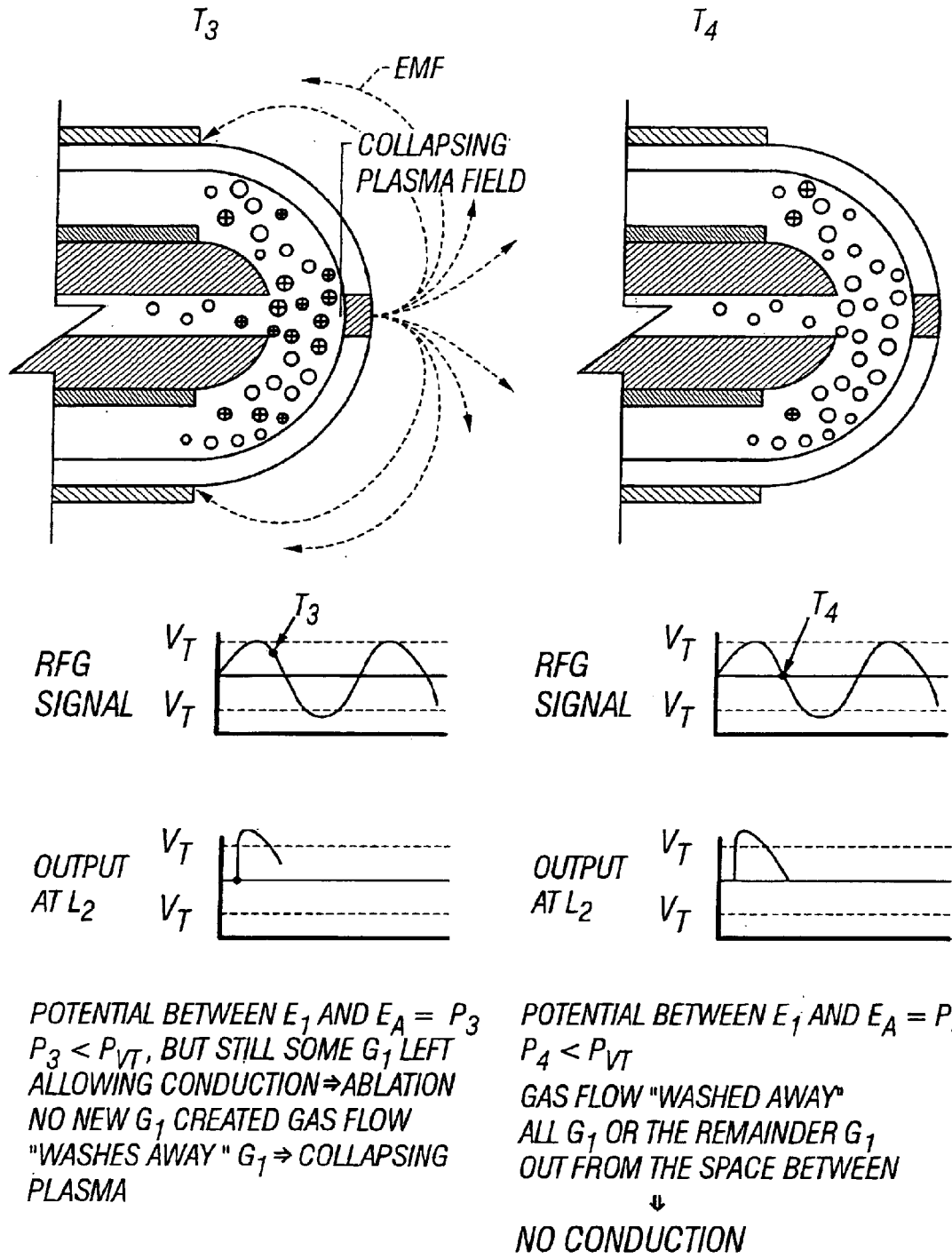
Figure 17:
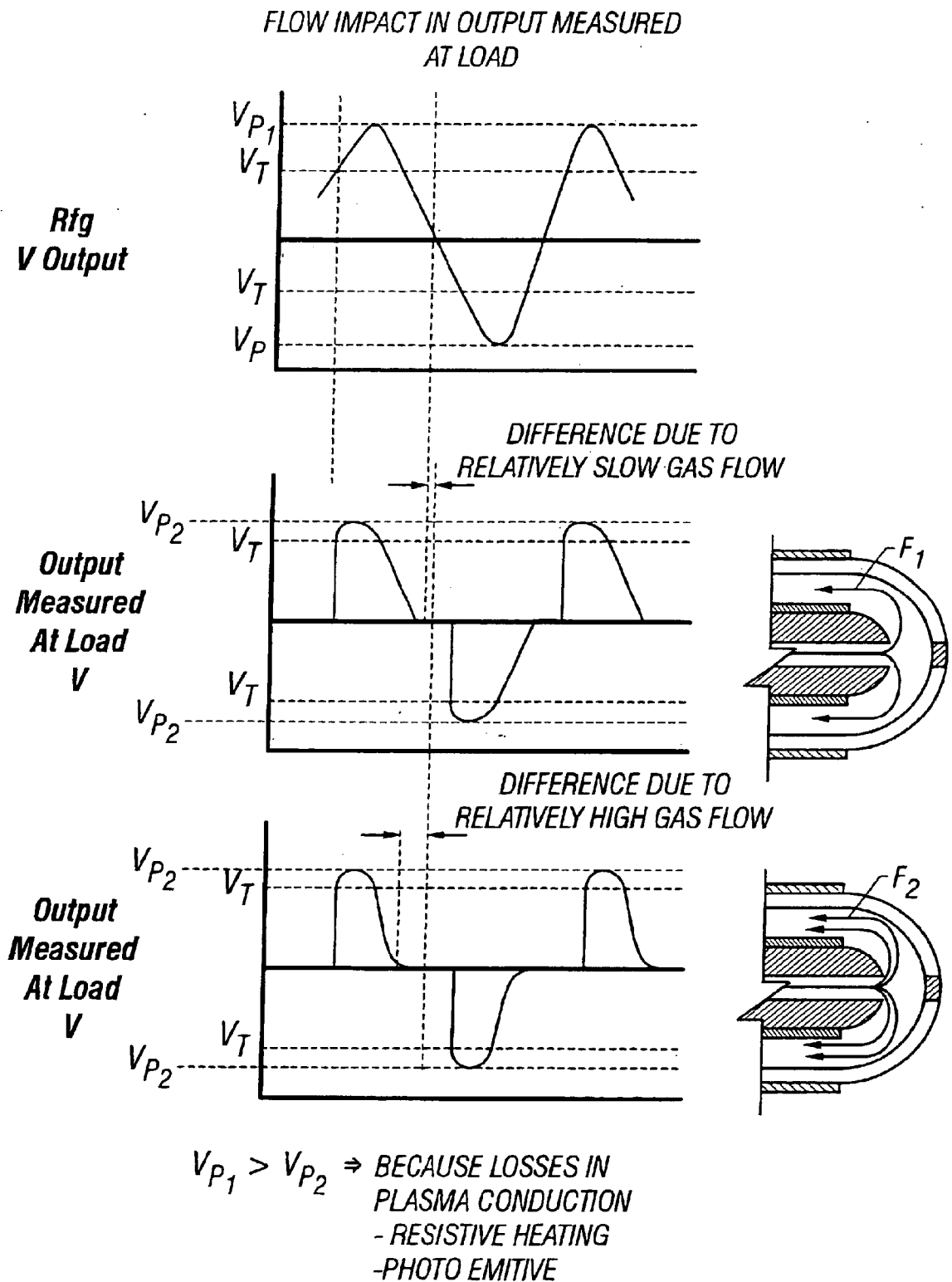
FIG. 17 is a series of plots graphically illustrating the impact of argon flow on the ablation device output at the body tissue/fluid load.

It should be noted that different gases will have different threshold voltages when used under identical conditions. Thus, during use of the present invention the user may select a gas for the spark gap switch that will have a desired threshold voltage. A single type of gas (e.g. argon) may be circulated through the system, or a plurality of gases may be mixed by a mixer pump 1031*a* as shown in FIG. 15C, for circulation through the system. Mixing of gases is desirable in that it allows a gas mixture to be created that has a threshold voltage corresponding to the desired treatment voltage. In all of the systems using circulated gas, gas leaving the system may be recycled through, and/or exhausted from, the system after it makes a pass through the spark gap switch.

FIGS. 16A through 16D schematically illustrate the effect of circulating the argon gas through the device. Circulation preferably is carried out at a rate of approximately 0.1 liters/minute to 0.8 liters/minute.

Referring to FIG. 16A, during initial activation of the RF generator, the potential between internal electrode 1022 and ablation electrode 1032 is insufficient to create an argon plasma. Argon molecules are thus non-ionized, and the voltage measured at the load L is 0V. There is no conduction from electrode 1022 to electrode 1032 at this time.

FIG. 16B shows the load voltage measured from internal electrode 1022 across the body fluid/tissue to return electrode 1030. Once the RF generator voltage output reaches voltage threshold $V_T$ of the argon, argon molecules are ionized to create a plasma. A stream of the ionized molecules flows from electrode 1022 to electrode 1032 and current is conducted from electrode 1032 to the tissue. Because the argon is flowing, some of the ionized molecules are carried away. Nevertheless, because of the high voltage, the population of ionized molecules is increasing at this point, and more than compensates for those that flow away, causing an expanding plasma within the device.

After the RF generator voltage falls below $V_T$, ion generation stops. Ionized molecules within the argon pool flow away as the argon is circulated, and others of the ions die off. Thus, the plasma begins collapsing and conduction to the ablation electrodes decreases and eventually stops. The process then repeats as the RF generator voltage approaches ($-V_T$) during the negative phase of its sinusoidal cycle.

Circulating the argon minimizes the number of ionized molecules that remain in the space between electrode 1022 and electrode 1032. If a high population of ionized molecules remained in this region of the device, their presence would result in conduction throughout the cycle, and the voltage at the tissue/fluid load L would eventually resemble the sinusoidal output of the RF generator. This continuous conduction at low voltages would result in collateral heating of the tissue.

Naturally, the speed with which ionized molecules are carried away increases with increased argon flow rate. For this reason, there will be more straightening of the trailing edge of the ablation waveform with higher argon flow rates than with lower argon flow rates. This is illustrated graphically in FIG. 17. The upper waveform shows the RF generator output voltage. The center waveform is the voltage output measured across the load (i.e. from the external electrode 1032 across the body tissue/fluid to the return electrode 1030) for a device in which the argon gas is slowly circulated. The lower waveform is the voltage output measured across the load for a device in which the argon gas is rapidly circulated. It is evident from the FIG. 17 graphs that the sloped trailing edge of the ablation waveform remains when the argon is circulated at a relatively low flow rate, whereas the trailing edge falls off more steeply when a relatively high flow rate is utilized. This steep trailing edge corresponds to minimized current conduction during low voltage phases. Flow rates which achieve the maximum benefit of straightening the trailing edge of the waveform are preferable. It should be noted that flow rates that are too high can interfere with conduction by flushing too many ionized molecules away during phases of the cycle when the output is at the threshold voltage. Optimal flow rates will depend on other physical characteristics of the device, such as the spark gap distance and electrode arrangement.

It should also be noted that the distance between internal electrode 1022 and external electrode 1032 also has an effect on the trailing edge of the ablation potential waveform. In the graphs of FIG. 18, the RF generator output is shown in the upper graph. $VP_{PRFG}$ represents the peak voltage output of the RF generator, $V_{T1}$ represents the voltage threshold of a device having a large separation distance (e.g. approximately 1 mm) between electrodes 1022 and 1032, and $V_{T2}$ represents the voltage threshold of a device in which electrodes 1022, 1032 are closely spaced—by a distance of approximately 0.1 mm. As previously explained, there is a higher voltage threshold in a device with a larger separation distance between the electrodes. This is because there is a large population of argon molecules between the electrodes 1022, 1032 that must be stripped of electrons before plasma conduction will occur. Conversely, when the separation distance between electrodes 1022 and 1032 is small, there is a smaller population of argon molecules between them, and so less energy is needed to ionize the molecules to create plasma conduction.

When the RF generator output falls below the threshold voltage, the molecules begin to deionize. When there are fewer ionized molecules to begin with, as is the case in configurations having a small electrode separation distance, the load voltage is more sensitive to the deionization of molecules, and so the trailing edge of the output waveform falls steeply during this phase of the cycle.

For applications in which a low voltage threshold is desirable, the device may be configured to have a small electrode spacing (e.g. in the range of 0.001–5 mm, most preferably 0.05–0.5 mm) and non-circulating argon. As discussed, doing so can produce a load output waveform having a steep rising edge and a steep falling edge, both of which are desirable characteristics. If a higher voltage threshold is needed, circulating the argon in a device with close inter-electrode spacing will increase the voltage threshold by increasing the pressure of the argon. Doing so will yield a highly dense population of charged ions during the phase of the cycle when the RF generator voltage is above the threshold voltage, but the high flow rate will quickly wash many ions away, causing a steep decline in the output waveform during the phases of the cycle when the RF generator voltage is below the threshold.

Figure 19:
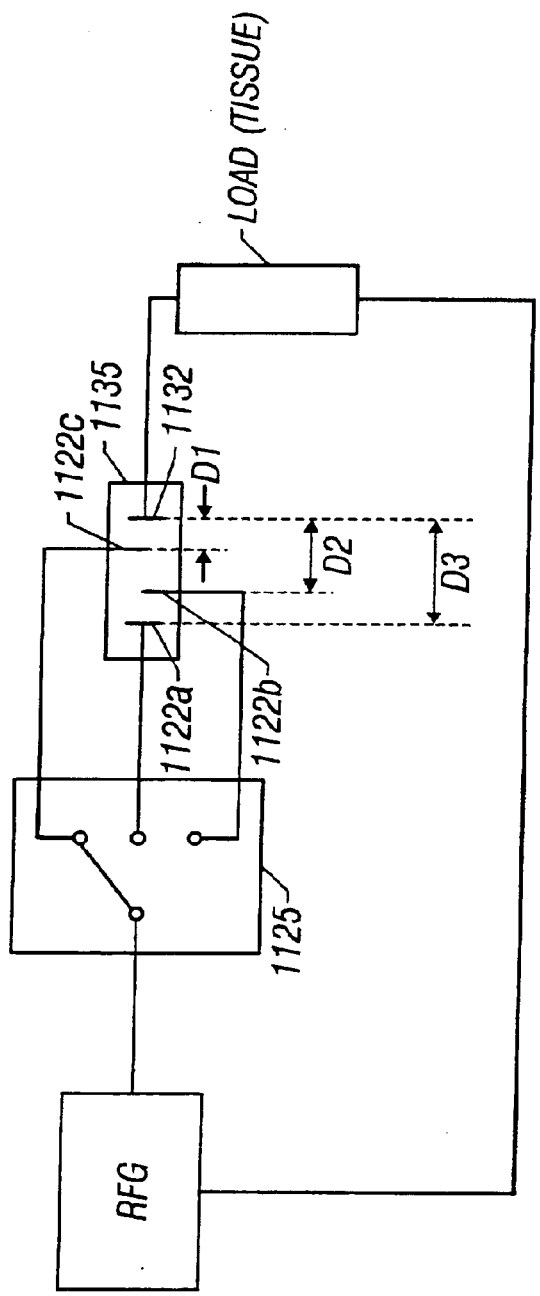
FIG. 19 is a schematic illustration of a twelfth embodiment of a system utilizing principles of the present invention, in which a spark gap spacing may be selected so as to pre-select a threshold voltage.

A twelfth embodiment of a system utilizing principles of the present invention is shown schematically in FIG. 19. The twelfth embodiment allows the threshold voltage to be adjusted by permitting the spark gap spacing (i.e. the effective spacing between the internal electrode and the patient contact electrode) to be selected. It utilizes a gas-filled spark gap switch having a plurality of internal electrodes 1122a, 1122b, 1122c. Each internal electrode is spaced from patient contact electrode 1132 by a different distance, D1, D2, D3, respectively. An adjustment switch 1025 allows the user to select which of the internal electrodes 1122a, 1122b, 1122c to utilize during a procedure. Since the threshold voltage of a spark gap switch will vary with the distance between the internal electrode and the contact electrode, the user will select an internal electrode which will set the spark gap switch to have the desired threshold voltage. If a higher threshold voltage is used, electrode 1022a will be utilized, so that the larger spark gap spacing D1 will give a higher threshold voltage. Conversely, the user will selected electrode 1022c, with the smaller spark gap spacing, if a lower threshold voltage is needed.

Several embodiments of voltage threshold ablation systems, and methods of using them, have been described herein. It should be understood that these embodiments are described only by way of example and are not intended to limit the scope of the present invention. Modifications to these embodiments may be made without departing from the scope of the present invention, and features described in connection with some of the embodiments may be combined with features described in others of the embodiments. It is intended that the scope of the invention is to be construed by the language of the appended claims, rather than by the details of the disclosed embodiments.

Any and all patents, patent applications and printed publications referred to above are incorporated by reference.

What is claimed is:

1. An electrosurgical device, for use with an oscillating electrical generator, for treating target tissue comprising:
    a proximal portion;
    a distal portion comprising:
        an insulated housing having an outer surface and an opening impervious to liquid and solid material formed therein; and
        a treatment electrode, the treatment electrode comprising an outer electrode surface exposed through the opening and positioned inwardly of the outer surface of the housing, whereby during use a gap is created between the outer electrode surface and target tissue so that target tissue does not touch the outer electrode surface;
    an electrical pathway, along at least the proximal and distal portions, electrically coupleable to the generator and extending at least through the gap; and
    the electrical pathway comprising a voltage threshold switch, the switch having a threshold voltage to prevent conduction of current along the electrical pathway and to the treatment electrode until the voltage across the switch reaches a threshold voltage.

2. The device according to claim 1 wherein the insulated housing comprises a plurality of said openings and the treatment electrode comprises a plurality of said outer electrode surfaces.

3. The device according to claim 1 wherein the treatment electrode comprises a hollow member surrounded by the housing.

4. The device according to claim 3 wherein the insulated housing comprises a plurality of openings formed therein with a plurality of the regions of the treatment electrode exposed through the plurality of openings.

5. The device according to claim 1 further comprising means for preventing a liquid or tissue from contacting the outer electrode surface during use.

6. The device according to claim 1 further comprising a movable insulation member movably positioned relative to the treatment electrode so to selectively cover a portion of the electrode outer surface to affect power transmission through the treatment electrode.

7. The device according to claim 6 wherein the insulation member comprises at least one of the following materials: polyimide, PTFE, glass, ceramic.

8. The device according to claim 1 wherein the voltage threshold switch comprises a spark gap switch.

9. The device according to claim 8 wherein the spark gap switch is located along the distal portion.

10. The device according to claim 8 wherein the spark gap switch comprises a gas reservoir containing a gas.

11. The device according to claim 10 wherein the gas reservoir is a fixed volume gas reservoir.

12. The device according to claim 10 wherein the spark gap switch comprises an intermediate electrode in contact with the gas reservoir.

13. The device according to claim 12 wherein the treatment electrode is in contact with the gas reservoir.

14. The device according to claim 12 wherein the intermediate electrode is at a fixed position within the gas reservoir.

15. The device according to claim 12 wherein the treatment electrode and the intermediate electrode have exposed surface areas and are in contact with the gas, said areas sized to control current density between the intermediate electrode and the treatment electrode.

16. The device according to claim 10 wherein the gas reservoir is defined by liquid-impervious structure.

17. The device according to claim 10 further comprising means for preventing liquid from entering the gas reservoir.

18. The device according to claim 1 further comprising means for cooling said treatment electrode.

19. The device according to claim 1 further comprising means for adjusting the current flow through said treatment electrode.

20. The device according to claim 1 further comprising means for automatically adjusting the current flow through said treatment electrode.

21. An electrosurgical device, for use with an oscillating electrical generator, for treating target tissue comprising:
    a proximal portion;
    a distal portion comprising an electrically insulating tissue-contacting surface and a treatment electrode, the treatment electrode comprising an electrode outer surface spaced-apart inwardly of the tissue-contacting surface so to create a gap between the electrode outer surface and target tissue during use;
    an electrical pathway electrically coupleable to the generator and extending at least through the gap;
    the electrical pathway comprising a voltage threshold switch, the switch having a threshold voltage to prevent conduction of current along the electrical pathway until the voltage across the switch reaches a threshold voltage;
    the voltage threshold switch comprising a spark gap switch, the spark gap switch comprising a gas reservoir within the distal portion and an intermediate electrode in contact with the gas reservoir; and
    the distal portion further comprises means for preventing liquid from entering the gas reservoir.

22. An electrosurgical device, for use with an oscillating electrical generator, for treating target tissue comprising:
    a proximal portion;
    a distal portion comprising a treatment electrode and means for preventing the treatment electrode from contacting target tissue during use;
    an electrical pathway electrically coupleable to the generator and extending at least through the treatment electrode; and
    the electrical pathway comprising a voltage threshold switch, the switch having a threshold voltage to prevent conduction of current along the electrical pathway until the voltage across the switch reaches a threshold voltage.

23. The device according to claim 22 wherein the voltage threshold switch comprises a spark gap switch, the spark gap switch comprising a gas reservoir within the distal portion and an intermediate electrode in contact with the gas reservoir, and wherein the distal portion further comprises means for preventing liquid from entering the gas reservoir.

* * * * *